(12) United States Patent
Little, II et al.

(10) Patent No.: US 6,906,037 B2
(45) Date of Patent: *Jun. 14, 2005

(54) THERAPEUTIC PEPTIDE-BASED CONSTRUCTS

(75) Inventors: Roger G. Little, II, Benicia, CA (US); Jong-Jye Lin, Hercules, CA (US)

(73) Assignee: Xoma Technology Ltd. (BM)

( * ) Notice: Subject to any disclaimer, the term of this patent is extended or adjusted under 35 U.S.C. 154(b) by 0 days.

This patent is subject to a terminal disclaimer.

(21) Appl. No.: 10/359,013

(22) Filed: Feb. 4, 2003

(65) Prior Publication Data

US 2004/0048793 A1 Mar. 11, 2004

Related U.S. Application Data

(63) Continuation of application No. 09/344,219, filed on Jun. 25, 1999, now Pat. No. 6,515,104.

(51) Int. Cl.[7] .............................................. A61K 38/10
(52) U.S. Cl. .............................. 514/14; 514/15; 514/16
(58) Field of Search ................................ 514/9, 12, 14, 514/15, 16; 530/326, 327, 328

(56) References Cited

U.S. PATENT DOCUMENTS

| | | | | |
|---|---|---|---|---|
| 5,639,727 A | * | 6/1997 | Little, II | 514/12 |
| 6,423,825 B1 | * | 7/2002 | Little et al. | 530/326 |
| 6,515,104 B1 | * | 2/2003 | Little et al. | 530/327 |

FOREIGN PATENT DOCUMENTS

WO   WO 97/04008   *   2/1997

OTHER PUBLICATIONS

Lehninger et al. Biochemistry, 2d ed. (1993), pp. 112–116 154–155.*

* cited by examiner

*Primary Examiner*—Jeffrey Edwin Russel
(74) *Attorney, Agent, or Firm*—McAndrews, Held & Malloy, Ltd.

(57) ABSTRACT

The present invention relates generally to small peptide-based constructs and their therapeutic uses. The sequences of these peptide-based constructs are based on a reverse subsequence derived from Domain II of bactericidal/permeability-increasing protein (BPI).

16 Claims, No Drawings

THERAPEUTIC PEPTIDE-BASED CONSTRUCTS

This a continuation of U.S. application Ser. No. 09/344,219, filed Jun. 25, 1999, now U.S. Pat. No. 6,515,104, incorporated by reference in its entirety.

FIELD OF THE INVENTION

The present invention relates generally to small peptide-based constructs that have 8 to 15 amino acid moieties. The sequences of these peptide-based constructs are designed and prepared based on a reverse subsequence (99–85) derived from amino acids identified and selected from Domain II of bactericidal permeability-increasing protein (BPI). The invention further relates to therapeutic uses of such peptide-based constructs due to their properties of heparin binding and neutralization, inhibition of endothelial cell proliferation and/or inhibition of angiogenesis, e.g., inhibition of in vivo neovascularization, including in models of chronic inflammatory disease states and metastatic tumors.

BACKGROUND OF THE INVENTION

Bactericidal/permeability-increasing protein (BPI) is a protein isolated from the granules of mammalian polymorphonuclear neutrophils (PMNs), which are blood cells essential in defending a mammal against invading microorganisms. Human BPI has been isolated from PMNs by acid extraction combined with either ion exchange chromatography (Elsbach, 1979, J. Biol. Chem. 254: 11000) or E. coli affinity chromatography (Weiss et al., 1987, Blood 69: 652), and has bactericidal activity against gram-negative bacteria. The molecular weight of human BPI is approximately 55,000 daltons (55 kD). The amino acid sequence of the entire human BPI protein and the nucleic acid sequence of DNA encoding BPI, have been reported by Gray et al., 1989, J. Biol. Chem. 264: 9505 (see FIG. 1 in Gray et al.). The Gray et al. DNA and amino acid sequences are set out in SEQ ID NOS: 12 and 13 hereto.

The bactericidal effect of BPI was originally reported to be highly specific to sensitive gram-negative species. The precise mechanism by which BPI kills gram-negative bacteria is not yet known, but it is known that BPI must first attach to the surface of susceptible gram-negative bacteria. This initial binding of BPI to the bacteria involves electrostatic interactions between BPI, which is a basic (i.e., positively charged) protein, and negatively charged sites on lipopolysaccharides (LPS). LPS is also known as "endotoxin" because of the potent inflammatory response that it stimulates. LPS induces the release of mediators by host inflammatory cells which may ultimately result in irreversible endotoxic shock. BPI binds to Lipid A, the most toxic and most biologically active component of LPS.

BPI is also capable of neutralizing the endotoxic properties of LPS to which it binds. Because of its gram-negative bactericidal properties and its ability to bind to and neutralize LPS, BPI can be utilized for the treatment of mammals suffering from diseases and conditions initiated by infection with gram-negative bacteria whether the bacteria infect from outside the host or the bacteria infect from within the host (i.e., gut-derived), including conditions of bacteremia, endotoxenia, and sepsis. These properties of BPI make BPI particularly useful and advantageous for such therapeutic administration.

A proteolytic fragment corresponding to the amino-terminal portion of human BPI possesses the LPS binding and neutralizing activities and antibacterial activity of BPI holoprotein. In contrast to the amino-terminal portion, the carboxyl-terminal region of isolated human BPI displays only slightly detectable antibacterial activity and some endotoxin neutralizing activity (Ooi et al., 1991, J. Exp. Med. 174: 649). One BPI amino-terminal fragment, referred to as "rBPI$_{23}$" (see Gazzano-Santoro et al., 1992, Infect. Immun. 60: 4754–4761) has been produced by recombinant means as a 23 kD protein and comprises an expression product of DNA encoding the first 199 amino acid residues of the human BPI holoprotein taken from Gray et al., supra, except that valine at position 151 is specified by GTG rather than GTC and residue 185 is glutamic acid (specified by GAG) rather than lysine (specified by AAG). Recombinant holoprotein, also referred to as rBPI, has also been produced having the sequence set out in SEQ ID NOS: 12 and 13 taken from Gray et al., supra, with the exceptions noted for rBPI$_{23}$. An N-terminal fragment analog designated rBPI$_{21}$ or rBPI$_{21}$Δcys or rBPI (1–193) ala$^{132}$ has been described in co-owned U.S. Pat. No. 5,420,019 and corresponding International Publication No. WO 94/18323 (PCT/US94/01235). This analog comprises the first 193 amino acids of BPI holoprotein as set out in SEQ ID NOS: 12 and 13 but wherein the cysteine at residue number 132 is substituted with alanine, and with the exceptions noted for rBPI$_{23}$. rBPI$_{23}$, as well as the cysteine substitution analog designated rBPI$_{21}$, have been introduced into human clinical trials. Proinflammatory responses to endotoxin were significantly ameliorated when rBPI$_{23}$ was administered in humans challenged with endotoxin. (See, e.g., co-owned U.S. Pat. Nos. 5,643,875 and 5,753,620 and corresponding International Publication No. WO 95/19784 (PCT/US95/01151). In addition, rBPI$_{21}$ was administered in humans with meningococcemia and hemorrhage due to trauma. (See, e.g., U.S. Pat. No. 5,888,977 and corresponding International Publication No. WO 97/42966 (PCT/US97/08016) and U.S. Pat. No. 5,756,464 and corresponding International Publication No. WO 97/44056 (PCT/US97/08941).

Other endotoxin binding and neutralizing proteins and peptides are known in the art. One example is Limulus antilipopolysaccharide factor (LALF) from horseshoe crab amebocytes (Warren et al., 1992, Infect. Immunol. 60: 2506–2513). Another example is a cyclic, cationic lipopeptide from Bacillus polymyxa, termed Polymyxin B$_1$. Polymyxin B$_1$ is composed of six α,γ-diaminobutyric acid residues, one D-phenylalanine, one leucine, one threonine and a 6-methyloctanoyl moiety (Morrison and Jacobs, 1976, Immunochem. 13: 813–818) and is also bactericidal. Polymyxin analogues lacking the fatty acid moiety are also known, which analogues retain LPS binding capacity but are without appreciable bactericidal activity (Danner et al., 1989, Antimicrob. Agents Chemother. 33: 1428–1434). Similar properties have also been found with synthetic cyclized polymyxin analogues (Rustici et al., 1993, Science 259: 361–365).

Known antibacterial peptides include cecropins and magainins. The cecropins are a family of antibacterial peptides found in the hemolymph of lepidopteran insects (Wade et al, 1990, Proc. Natl. Acad. Sci. USA 87: 4761–4765), and the magainins are a family of antibacterial peptides found in Xenopus skin and gastric mucosa (Zasloffet al., 1988, Proc. Natl. Acad. Sci. USA 85: 910–913). These peptides are linear and range from about 20 to about 40 amino acids in length. A less active mammalian cecropin has been reported from porcine intestinal mucosa, cecropin P1 (Boman et al., 1993, Infect. Immun. 61: 2978–2984). The cecropins are generally reported to be more potent than the magainins in bactericidal activity and appear to have less mammalian cell cytotoxicity. The cecropins and magainins are characterized by a continuous, amphipathic α-helical region which is necessary for bactericidal activity. The most potent of the cecropins identified to date is cecropin with the BPI amino acid sequence 90–99 but does not share the motif of charged and uncharged amino acids specified by the BPI amino acid sequence 90–99. In addition, the other 27 amino acids of cecropin A are necessary for maximal bactericidal activity and there is no homology with BPI for those 27 amino acids. The magainins have minimal homology with the BPI amino acid sequence 90–99.

Of interest to the present application are the disclosures in PCT International Application PCT/US91/05758 [WO 92/03535] relating to compositions comprising BPI and an anionic compound, which compositions are said to exhibit (1) no bactericidal activity and (2) endotoxin neutralizing activity. Anionic compounds are preferably a protein such as serum albumin but can also be a polysaccharide such as heparin. In addition, Weiss et al., 1975, *J. Clin. Invest.* 55: 33–42, disclose that heparin sulfate and LPS block expression of the permeability-increasing activity of BPI. However, neither reference discloses that BPI actually binds to and/or neutralizes the biologic activities of heparin. Heparin binding does not necessarily imply heparin neutralization. For example, a family of heparin binding growth factors (HBGF) requires heparin as a cofactor to elicit a biological response. Examples of HBGF's include: fibroblast growth factors (FGF-1, FGF-2) and endothelial cell growth factors (ECGF-1, ECGF-2). Antithrombin III inhibition of clotting cascade proteases is another example of a heparin binding protein that requires heparin for activity and clearly does not neutralize heparin. Heparin binding proteins that do neutralize heparin (e.g., platelet factor IV, protanune, and thrombospondin) are generally inhibitory of the activities induced by heparin binding proteins that use heparin as a cofactor.

Of particular interest to the present application are the heparin-related activities of BPI protein products. Specifically, BPI protein products have been shown to have heparin binding and heparin neutralization activities in co-assigned U.S. Pat. Nos. 5,348,942; 5,639,727; 5,807,818; 5,837,678; 5,854,214 and corresponding International Publication No. WO 94/02401 (PCT/US94/02401). For example, rBPI$_{23}$ was shown to have high affinity for heparin (see also, Little et al., 1994, *J. Biol. Chem.* 269: 1865–1872, and has been administered in humans to neutralize heparin (see, e.g. U.S. Pat. No. 5,348,942). These heparin binding and neutralization activities of BPI protein products are significant due to the importance of current clinical uses of heparin. Heparin is commonly administered in doses of up to 400 U/kg during surgical procedures such as cardiopulmonary bypass, cardiac catheterization and hemodialysis procedures in order to prevent blood coagulation during such procedures. When heparin is administered for anticoagulant effects during surgery, it is an important aspect of post-surgical therapy that the effects of heparin are promptly neutralized so that normal coagulation function can be restored. Currently, protamine is used to neutralize heparin. Protamines are a class of simple, arginine-rich, strongly basic, low molecular weight proteins. Administered alone, protamines (usually in the form of protamine sulfate) have anti-coagulant effects. When administered in the presence of heparin, a stable complex is formed and the anticoagulant activity of both drugs is lost. However, significant hypotensive and anaphylactoid effects of protamine have limited its clinical utility. Thus, due to its heparin binding and neutralization activities, BPI protein products have potential utility as a substitute for protamine in heparin neutralization in a clinical context without the deleterious side-effects which have limited the usefulness of the protamines. The additional antibacterial and anti-endotoxin effects of such BPI protein products would also be useful and advantageous in post-surgical heparin neutralization compared with protamine.

Additionally of particular interest, is the activity of BPI protein products to inhibit angiogenesis due in part to their heparin binding and neutralization activities (see, e.g., U.S. Pat. Nos. 5,807,818 and 5,837,678 and corresponding International Publication No. WO 94/02401 (PCT/US94/02401). Angiogenesis, the growth of new blood vessels (neovascularization) is a complex phenomenon that involves growth factors, most of which have heparin as a co-factor. In adults, angiogenic growth factors are released as a result of vascular trauma (wound healing), immune stimuli (autoimmune disease), inflammatory mediators (prostaglandins) or from tumor cells. These factors induce proliferation of endothelial cells (which is necessary for angiogenesis) via a heparin-dependent receptor binding mechanism (see Yayon et al., 1991, *Cell* 64: 841–848). Angiogenesis is also associated with a number of other pathological conditions, including the growth, proliferation, and metastasis of various tumors; diabetic retinopathy, macular degeneration, retrolental fibroplasia, neovascular glaucoma, psoriasis, angiofibromas, immune and non-immune inflammation including rheumatoid arthritis, capillary proliferation within atherosclerotic plaques, hemangiomas, endometriosis and Kaposi's sarcoma. Thus, it would be desirable to inhibit angiogenesis in these and other instances, and the heparin binding and neutralization activities of BPI protein products, including peptides derived from or based on BPI, are useful to that end.

Heparin binding proteins fall into at least two classes. The first class consists of those proteins that utilize heparin as a co-factor in eliciting a specific response. These proteins include heparin-dependent growth factors (e.g., basic fibroblast growth factor, acidic fibroblast growth factor and vascular endothelial cell growth factor) which play a major role in angiogenesis. The second class includes proteins that neutralize the heparin-dependent response. BPI protein products, including peptides derived from BPI, have been identified as heparin neutralizing and anti-angiogenic agents. Several other heparin neutralizing proteins are also known to inhibit angiogenesis. For example, protamine is known to inhibit tumor-associated angiogenesis and subsequent tumor growth [see Folkman et al., 1992, *Inflammation: Basic Principles and Clinical Correlates*, 2d ed., (Galin et al., eds., Review Press, N.Y.), Ch. 40, pp. 821–839]. A second heparin neutralizing protein, platelet factor IV, also inhibits angiogenesis (i.e., is angiostatic). Another known angiogenesis inhibitor, thrombospondin, binds to heparin with a repeating serine/tryptophan motif instead of a basic amino acid motif (see Guo et al., 1992, *J. Biol. Chem.* 267: 19349–19355). Murine endostatin is also reported to bind heparin and inhibit angiogenesis (see, e.g., Hohenester et al., 1998, *Embo J.* 17: 1656–1664; O'Reilly et al, 1997, *Cell* 88: 277–285).

Another utility of BPI protein products involves pathological conditions associated with chronic inflammation, which is usually accompanied by angiogenesis (see, e.g., U.S. Pat. No. 5,639,727). One example of a human disease related to chronic inflamation is arthritis, which involves inflammation of peripheral joints. In rheumatoid arthritis, the inflammation is autoimmune, while in reactive arthritis, inflammation is hypothesized to be associated with initial infection of the synovial tissue with pyogenic bacteria or other infectious agents followed by aseptic chronic inflammation in susceptible individuals. Folkman et al., 1992, supra, have also noted that many types of arthritis progress from a stage dominated by an inflammatory infiltrate in the joint to a later stage in which a neovascular pannus invades the joint and begins to destroy cartilage. While it is unclear whether angiogenesis in arthritis is a causative component of the disease or an epiphenomenon, there is evidence that angiogenesis is necessary for the maintenance of synovitis in rheumatoid arthritis. One known angiogenesis inhibitor, AGM1470, has been shown to prevent the onset of arthritis and to inhibit established arthritis in collagen-induced arthritis models (Peacock et al., 1992, *J. Exp. Med.* 175: 1135–1138). While nonsteroidal anti-inflammatory drugs, corticosteroids and other therapies have provided treatment improvements for relief of arthritis, there remains a need in the art for more effective therapies for arthritis and other inflammatory diseases.

Many additional utilities of BPI protein products, including rBPI$_{23}$ and rBPI$_{21}$, have been described due to the wide variety of biological activities of these products. For example, BPI protein products are bactericidal for gram-negative bacteria, as described in U.S. Pat. Nos. 5,198,541 and 5,523,288. International Publication No. WO 94/20130 proposes methods for treating subjects suffering from an infection (e.g. gastrointestinal) with a species from the gram-negative bacterial genus *Helicobacter* with BPI protein products. BPI protein products also enhance the effectiveness of antibiotic therapy in gram-negative bacterial infections, as described in U.S. Pat. No. 5,523,288 and International Publication No. WO 95/08344 (PCT/US94/11255). BPI protein products are also bactericidal for gram-positive bacteria and mycoplasma, and enhance the effectiveness of antibiotics in gram-positive bacterial infections, as described in U.S. Pat. Nos. 5,578,572 and 5,783,561 and International Publication No. WO 95/19180 (PCT/US95/00656). BPI protein products exhibit anti-fungal activity, and enhance the activity of other anti-fungal agents, as described in U.S. Pat. No. 5,627,153 and International Publication No. WO 95/191 79 (PCT/US95/00498). and further as described for anti-fungal peptides in U.S. Pat. No. 5,858,974, which is in turn a continuation-in-part of U.S. application Ser. No. 08/504,841, abandoned, and corresponding International Publication Nos. WO 96/08509 (PCT/US95/09262) and WO 97/04008 (PCT/US96/03845). BPI protein products exhibit anti-protozoan activity, as described in U.S. Pat. No. 5,646,114 and International Publication No. WO 96/01 647 (PCT/US95/08624). BPI protein products exhibit anti-chlamydial activity, as described in co-owned U.S. Pat. No. 5,888,973 and WO 98/06415 (PCT/US97/13810). Finally, BPI protein products exhibit anti-mycobacterial activity, as described in co-owned, co-pending U.S. application Ser. No. 08/626,646, issued as U.S. Pat. No. 6,214,789, which is in turn a continuation of U.S. application Ser. No. 08/285,803, abandoned, which is in turn a continuation-in-part of U.S. application Ser. No. 08/031,145, abandoned, and corresponding International Publication No. WO 94/20129 (PCT/U594/02463).

The effects of BPI protein products in humans on endotoxin in circulation, including effects on TNF, IL-6 and endotoxin are described in U.S. Pat. No. 5,643,875 and corresponding International Publication No. WO 95/19784 (PCT/US95/01151).

BPI protein products are also useful for treatment of specific disease conditions, such as meningococcemia in humans (as described in co-owned U.S. application Ser. No. 08/644,287 and U.S. Pat. No. 5,888,977 and International Publication No. WO97/42966 (PCT/US97/08016), hemorrhagic trauma in humans, (as described in U.S. Pat. No. 5,756,464, U.S. application Ser. No. 08/862,785 and corresponding International Publication No. WO 97/44056 (PCT/US97/08941), burn injury (as described in U.S. Pat. No. 5,494,896) ischemia/reperfusion injury (as described in U.S. Pat. No. 5,578,568), and liver resection (as described in co-owned, co-pending U.S. application Ser. No. 08/582,230 which is in turn a continuation of U.S. application Ser. No. 08/318,357, which is in turn a continuation-in-part of U.S. application Ser. No. 08/132,510, and corresponding International Publication No. WO 95/10297 (PCT/US94/11404).

BPI protein products are also useful in antithrombotic methods, as described in U.S. Pat. No. 5,741,779 and U.S. application Ser. No. 09/063,465 and corresponding International Publication No. WO 97/42967 (PCT/US7/08017).

There continues to exist a need in the art for new products that have one or more of the biological activities of BPI protein products, particularly products for use as heparin binding and neutralizing agents and for the inhibition of endothelial cell proliferation as well as inhibition of angiogenesis (normal or pathological). Advantageous therapeutic products that are peptide-based would ideally comprise small active sequences that are serum stable.

SUMMARY OF THE INVENTION

This invention provides compounds and compositions of small peptide-based constructs having an 8–15 amino acid moiety sequence that is derived from or based on reverse subsequences from functional domain II (amino acids 65–99) of BPI and having at least one of the heparin-related biological activities of BPI, such as heparin binding, heparin neutralization, inhibition of endothelial cell proliferation and/or inhibition of angiogenesis. A reverse (or retro) sequence is inverted from the original (e.g., if an original sequence is A-B-C, the inverted sequence is C-B-A). Such peptide-based constructs according to the invention have reverse subsequences that consist of a minimum core sequence based on an amino acid motif derived from amino acids 99–92 of BPI. In a preferred embodiment the reverse subsequence is a substituted subsequence (for example, amino acids 99–92, 99–91, 99–90, 99–89, 99–88, 99–87, 99–86, or 99–85 wherein the substitutions are at 95 and 91).

Constructs (or compositions) according to the invention include those that are 8–15 moieties in length having heparin binding, heparin neutralizing, endothelial cell proliferation inhibiting, or antiangiogenic properties and comprise: a sequence having the formula: α-χ-χ-α-χ-β-χ-α-R. In the sequence, α is a hydrophilic basic amino acid moiety selected from the group consisting of lysine, arginine, histidine, ornithine, diaminobutyric acid, citrulline, or para-amino phenylalanine; β is a hydrophilic neutral amino acid moiety selected from the group consisting of asparagine, glutamine, serine, threonine, tyrosine, hydroxyproline, or 7-hydroxy-tetrahydroisoquinoline carboxylic acid; χ is a hydrophobic amino acid moiety selected from the group consisting of alanine, naphthylalanine, biphenylalanine, valine, leucine, isoleucine, proline, hydroxyproline, phenylalanine, tryptophan, methionine, glycine, cyclohexylalanine, amino-isobutyric acid, norvaline, norleucine, tert-leucine, tetrahydroisoquinoline carboxylic acid, pipecolic acid, phenylglycine, homophenylalanine, cyclohexylglycine, dehydroleucine, 2,2-diethylglycine, 1-amino-1-cyclopentane carboxylic acid, 1-amino-1- cyclohexane carboxylic acid, amino-benzoic acid, amino-naphthyl carboxylic acid, γ-amino butyric acid, beta-alanine, difluorophenylalanine, fluorophenylalanine, nipecotic acid, aminobutyric acid, thienyl-alanine, t-butyl-glycine; and R is a moiety selected from the group consisting of -χ, -χ-α, -χ-α-χ, χ-α-χ-β, -χ-α-χ-β-χ, -χ-α-χ-β-χ-α, -χ-α-χ-β-χ-α-χ, -χ-β-χ-χ-β-χ, —NH$_2$, -χ-NH$_2$, -χ-α-NH$_2$, -χ-α-χ-NH$_2$, -χ-α-χ-β-NH$_2$, -χ-α-χ-β-χ-NH$_2$, -χ-α-χ-β-χ-α-NH$_2$, -χ-α-NH$_2$,-χ-α-χ-β-χ-α-χ-NH$_2$, -χ-β-χ-χ-β-χ-NH$_2$.

The invention also provides a composition of 8–15 amino acid moieties consecutively linked by peptide bonds, said composition having heparin binding properties and comprising a sequence of the formula:

KLFR(naph-A)QAR$_1$ wherein R$_1$ is selected from the group consisting of K, K(naph-A), K(naph-A)K, K(naph-A)KG, K(naph-A)KGS, K(naph-A)KGSI, K(naph-A)KGSIK and K(naph-A)KGSIKI; and wherein the carboxyl terminal group is amidated or nonamidated, and conservative substitution variants thereof having heparin binding properties. Preferably, the variants comprise at least one conservative substitution.

The compositions of the invention preferably comprise compositions wherein the first two amino-terminal amino acid moieties are D-amino acid moieties and the last two carboxy-terminal amino acid moieties are D-amino acid moieties.

Also provided are methods of neutralizing heparin in a mammal that has been administered an exogenous heparin compound (including heparin or heparinoid substances, such as low molecular weight heparins) comprising the step of administering to said mammal an amount of the composition of the invention effective to neutralize the anticoagulant effect of the exogenous heparin compound, preferably in an amount effective to return the clotting time of said mammal to normal; methods of inhibiting endothelial cell proliferation in a mammal in need thereof by administering to said mammal an amount of the compositions of the invention effective to inhibit endothelial cell proliferation; methods of inhibiting angiogenesis in a mammal in need thereof by administering to said mammal an amount of such compositions effective to inhibit angiogenesis, including angiogenesis in the eye; methods of treating a mammal suffering from a disorder involving angiogenesis, including a chronic inflammatory disease, such as rheumatoid or reactive arthritis, and including the growth, proliferation or metastasis of tumor cells.

Additional properties or activities of such constructs may include LPS binding, LPS neutralization, and/or antimicrobial activity and/or any other previously known activity or property of BPI protein products. Although three functional domains of BPI were previously reported and include: domain I, encompassing the amino acid sequence of BPI from about amino acid 17 to about amino acid 45; domain-II, encompassing the amino acid sequence of BPI from about amino acid 65 to about amino acid 99; and domain III, encompassing the amino acid sequence of BPI from about amino acid 142 to about amino acid 169, biologically active reverse (or retro) sequences have not been previously reported based on subsequences of domain II. Thus, such peptide-based reverse (retro) sequence constructs according to the invention, which preferably comprise selected D-amino acid moieties, are particularly useful as therapeutic agents.

DETAILED DESCRIPTION

The present invention provides biologically active novel constructs (or compositions) having a sequence of 8 to 15 amino acid moieties that is derived from a reverse subsequence of functional domain II of BPI (i.e., peptide-based constructs). Preferred are constructs with sequences that contain D-amino acid moieties. Particularly preferred are constructs with sequences where the D-amino acid moieties are positioned as the first two and last two moieties of the sequence. Such constructs are particularly useful for the treatment of heparin-related or heparin-mediated disorders, diseases or conditions. "Treatment" as used herein encompasses both prophylactic and therapeutic treatment. Treatment of mammals, including humans, is contemplated.

As used herein, "amino acid moiety" includes typical and a typical amino acid compounds (including derivatized amino acids and amino acid analogs). "Conservative" substitutions of one amino acid for another are substitutions of amino acids having similar structural and/or chemical properties, and are generally based on simlarities in polarity, charge, hydrophobicity, hydrophilicity and/or the amphipathic nature of the residues involved. Hydrophobic, polar neutral and polar basic amino acids include those described above for α, β and χ. Polar acidic amino acids include aspartic acid and glutamic acid. As a general rule, as the similarity between the amino acids being substituted decreases, the likelihood that the substitution will affect activity increases.

For the purposes of this invention, the term "functional domain" is intended to designate a region of the amino acid sequence of BPI that exhibits one or more of the biological activities of BPI. These functional domains of BPI were defined by the activities of proteolytic cleavage fragments, overlapping 15-mer peptides and other synthetic peptides. Domain I has been defined as the amino acid sequence of BPI comprising from about amino acid 17 to about amino acid 45. Initial peptides based on this domain were moderately active in both the inhibition of LPS-induced LAL activity and in heparin binding assays, and did not exhibit significant antibacterial activity. Domain II has been defined as the amino acid sequence of BPI comprising from about amino acid 65 to about amino acid 99. Initial peptides based on this domain exhibited high LPS and heparin binding capacity and exhibited significant antibacterial activity. Domain III has been defined as the amino acid sequence of BPI comprising from about amino acid 142 to about amino acid 169. Initial peptides based on this domain exhibited high LPS and heparin binding activity, and exhibited surprising antimicrobial activity, including antifungal and antibacterial (including, e.g., anti-gram-positive and anti-gram-negative) activity.

For purposes of this invention, the term "biological activity of BPI" is intended to include, but is not limited to one or more of the biological activities or properties of a human bactericidal/permeability-increasing (BPI) protein product, including, for example, a recombinant BPI holoprotein such rBPI (SEQ ID NO: 13), an amino-terminal fragment of BPI such as rBPI$_{23}$, and analogs that are mutated amino-terminal fragments of BPI such as rBPI$_{21}$Δcys and including any of the known activities of the BPI protein products discussed above. Specifically included is a biological activity of any peptide-based construct of this invention that is between 0.1 and 10 times the activity of BPI or of a corresponding peptide encompassing a corresponding functional domain of BPI. The term "biological activity of BPI" is intended to include, but is not limited to an activity of heparin binding, heparin neutralization, inhibition of endothelial cell proliferation or inhibition of angiogenesis (e.g., inhibition of in vivo neovascularization such as that associated with metastatic tumors and chronic inflammatory disease states). Also included in this definition of "biological activity of BPI" is an activity of LPS binding, LPS neutralization, or antimicrobial activity. Also expressly included in this definition of the "biological activity of BPI" is a biological activity, for example antimicrobial activity, that is qualitatively different than the activity of BPI or the corresponding peptide encompassing the entire corresponding domain of BPI. For example, such qualitative differences include differences in the spectrum of bacteria or other microorganisms against which the peptide is effective, relative to the amino acid sequence of the corresponding functional domain of BPI. This definition thus encompasses antimicrobial activities, such as antibacterial activity (e.g., against gram-positive bacteria, mycobacteria and chlamydia) and antifungal activity (e.g., against species of *Candida, Aspergillus, Cryptococcus, Histoplasma, Coccidioides, Blastomyces, Basidiobolus, Conidiobolus, Rhizopus, Rhizomucor, Mucor, Absidia, Mortierella, Cunninghamella, Saksenaea, Fusarium, Trichophyton, Trichosporon, Microsporum, Epidermophyton, Scytalidium, Malassezia, Actinomyceies, Sporothrix* and *Penicillium*).

The invention provides exemplary peptide-based constructs each of which has a sequence that is derived from or based on reverse substituted subsequences from functional domain II of human BPI (e.g., amino acids 99–92, 99–91, 99–90, 99–89, 99–88, 99–87, 99–86, or 99–85 wherein the substitutions are at 75 and 91)). Embodiments of such constructs include the following exemplary domain II basic constructs [single-letter abbreviations for amino acids can be found in G. Zubay, *Biochemistry* (2d. ed.), 1988 (MacMillen Publishing: N.Y.), p.33]:

```
XMP.394 (1)                              (SEQ ID NO:1)
k-l-f-r-(naph-a)-q-a-k-(naph-a)-k-g-s-i-k-i XMP.624 (2)                              (SEQ ID NO:2)
k-l-f-r-(naph-a)-q-a-k-(naph-a)-k-g-s-i-k XMP.625 (3)                              (SEQ ID NO:3)
k-l-f-r-(naph-a)-q-a-k-(naph-a)-k-g-s-i XMP.626 (4)                              (SEQ ID NO:4)
k-l-f-r-(naph-a)-q-a-k-(naph-a)-k-g-s XMP.627 (5)                              (SEQ ID NO:5)
k-l-f-r-(naph-a)-q-a-k-(naph-a)-k-g XMP.628 (6)                              (SEQ ID NO:6)
k-l-f-r-(naph-a)-q-a-k-(naph-a)-k XMP.629 (7)                              (SEQ ID NO:7)
k-l-f-r-(naph-a)-q-a-k-(naph-a)

XMP.630 (8)                              (SEQ ID NO:8)
k-l-f-r-(naph-a)-q-a-k

XMP.656 (9)                              (SEQ ID NO:9)
k-l-f-r-(naph-a)-q-a-k-(naph-a)-k-g-i-k-i XMP.679 (10)                             (SEQ ID NO:10)
k-l-f-k-(naph-a)-q-a-k-(naph-a)-k-g XMP.684 (11)                             (SEQ ID NO:11)
(biphenyl-a)-k-l-f-r-(naph-a)-q-a-k
```

As used herein, "BPI protein product" includes naturally and recombinantly produced BPI protein; natural, synthetic, and recombinant biologically active polypeptide fragments of BPI protein; biologically active polypeptide variants of BPI protein or fragments thereof, including hybrid fusion proteins and dimers; biologically active polypeptide analogs of BPI protein or fragments or variants thereof, including cysteine-substituted analogs; and BPI-derived peptides. BPI protein products may be generated and/or isolated by any means known in the art. U.S. Pat. No. 5,198,541, discloses recombinant genes encoding, and methods for expression of, BPI proteins including recombinant BPI holoprotein, referred to as rBPI and recombinant fragments of BPI. U.S. Pat. No. 5,439,807 and corresponding International Publication No. WO 93/23540 (PCT/US93/04752), disclose novel methods for the purification of recombinant BPI protein products expressed in and secreted from genetically transformed mammalian host cells in culture and discloses how one may produce large quantities of recombinant BPI products suitable for incorporation into stable, homogeneous pharmaceutical preparations.

Biologically active fragments of BPI (BPI fragments) include biologically active molecules that have the same or similar amino acid sequence as a natural human BPI holoprotein, except that the fragment molecule lacks amino-terminal amino acids, internal amino acids, and/or carboxy-terminal amino acids of the holoprotein. Nonlimiting examples of such fragments include an N-terminal fragment of natural human BPI of approximately 25 kD, described in Ooi et al., 1991, *J. Exp. Med.,* 174:649, and the recombinant expression product of DNA encoding N-terminal amino acids from 1 to about 193 to 199 of natural human BPI, described in Gazzano-Santoro et al., 1992, *Infect. Immun.* 60:4754–4761, and referred to as $rBPI_{23}$. In that publication, an expression vector was used as a source of DNA encoding a recombinant expression product ($rBPI_{23}$) having the 31-residue signal sequence and the first 199 amino acids of the N-terminus of the mature human BPI, as set out in FIG. 1 of Gray et al., supra, except that valine at position 151 is specified by GTG rather than GTC and residue 185 is glutamic acid (specified by GAG) rather than lysine (specified by AAG). Recombinant holoprotein (rBPI) has also been produced having the sequence (SEQ ID NOS: 12 and 13) set out in FIG. 1 of Gray et al., supra, with the exceptions noted for $rBPI_{23}$ and with the exception that residue 417 is alanine (specified by GCT) rather than valine (specified by GTT). An analog of an N-terminal fragment consisting of residues 10–193 of BPI has been described in co-owned, co-pending U.S. application Ser. No. 09/099,725. Other examples include dimeric forms of BPI fragments, as described in U.S. Pat. No. 5,447,913 and corresponding International Publication No. WO 95/24209 (PCT/US95/03125).

Biologically active variants of BPI (BPI variants) include but are not limited to recombinant hybrid fusion proteins, comprising BPI holoprotein or biologically active fragment thereof and at least a portion of at least one other polypeptide, and dimeric forms of BPI variants. Examples of such hybrid fusion proteins and dimeric forms are described in U.S. Pat. No. 5,643,570 and corresponding International Publication No. WO 93/23434 (PCT/US93/04754), and include hybrid fusion proteins comprising, at the amino-terminal end, a BPI protein or a biologically active fragment thereof and, at the carboxy-terminal end, at least one constant domain of an immunoglobulin heavy chain or allelic variant thereof.

Biologically active analogs of BPI (BPI analogs) include but are not limited to BPI protein products wherein one or more amino acid residues have been replaced by a different amino acid. For example, U.S. Pat. No. 5,420,019 and corresponding International Publication No. WO 94/18323 (PCT/US94/01235), discloses polypeptide analogs of BPI and BPI fragments wherein a cysteine residue is replaced by a different amino acid. A stable BPI protein product described by this application is the expression product of DNA encoding from amino acid 1 to approximately 193 or 199 of the N-terminal amino acids of BPI holoprotein, but wherein the cysteine at residue number 132 is substituted with alanine and is designated rBPI$_{21}$Δcys or rBPI$_{21}$. Production of this N-terminal analog of BPI, rBPI$_{21}$, has been described in Horwitz et al., 1996, *Protein Expression Purification*, 8:28–40. Similarly, a fragment consisting of residues 10–193 of BPI in which the cysteine at position 132 is replaced with an alanine (designated "rBPI(10–193) C132A" or "rBPI(10–193)ala$^{132}$") has been described in co-owned, co-pending U.S. application Ser. No. 09/099,725. Other examples include dimeric forms of BPI analogs; e.g. U.S. Pat. No. 5,447,913 and corresponding International Publication No. WO 95/24209 (PCT/US95/03125).

Other BPI protein products are peptides derived from or based on BPI produced by synthetic or recombinant means (BPI-derived peptides), such as those described in International Publication No. WO 97/04008 (PCT/US96/03845), which corresponds to U.S. Pat. No. 5,858,974 and International Publication No. WO 96/08509 (PCT/US95/09262), which corresponds to U.S. patent application Ser. No. 09/119,858, and International Publication No. WO 95/19372 (PCT/US94/10427), which corresponds to U.S. Pat. Nos. 5,652,332 and 5,856,438, and International Publication No. WO94/20532 (PCT/US94/02465), which corresponds to U.S. Pat. No. 5,763,567 which is a continuation of U.S. Pat. No. 5,733,872, which is a continuation-in-part of U.S. application Ser. No. 08/183,222, which is a continuation-in-part of U.S. application Ser. No. 08/093,202 (corresponding to International Publication No. WO 94/20128 (PCT/US94/02401)), which is a continuation-in-part of U.S. Pat. No. 5,348,942, as well as International Publication No. WO 97/35009 (PCT/US97/05287), which corresponds to U.S. Pat. No. 5,851,802.

The present invention defines novel peptide-based constructs that may be defined as BPI protein products.

The administration of BPI protein products is preferably accomplished with a pharmaceutical composition comprising a BPI protein product and a pharmaceutically acceptable diluent, adjuvant, or carrier. The BPI protein product may be administered without or in conjunction with known surfactants or other therapeutic agents. A stable pharmaceutical composition containing BPI protein products (e.g., rBPI$_{23}$) comprises the BPI protein product at a concentration of 1 mg/ml in citrate buffered saline (5 or 20 mM citrate, 150 mM NaCl, pH 5.0) comprising 0.1% by weight of poloxamer 188 (Pluronic F-68, BASF Wyandotte, Parsippany, N.J.) and 0.002% by weight of polysorbate 80 (Tween 80, ICI Americas Inc., Wilmington, Del.). Another stable pharmaceutical composition containing BPI protein products (e.g., rBPI$_{21}$) comprises the BPI protein product at a concentration of 2 mg/ml in 5 mM citrate, 150 mM NaCl, 0.2% poloxamer 188 and 0.002% polysorbate 80. Such preferred combinations are described in U.S. Pat. Nos. 5,488,034 and 5,696,090 and corresponding International Publication No. WO 94/17819 (PCT/US94/01239). As described in U.S. Pat. No. 5,912,228, which is in turn a continuation-in-part of U.S. application Ser. No. 08/530,599, which is in turn a continuation-in-part of U.S. application Ser. No. 08/372,104, and corresponding International Publication No. WO 96/21436 (PCT/US96/01095), other poloxamer formulations of BPI protein products with enhanced activity may be utilized. Peptide-based constructs may be formulated like other BPI protein products or may be formulated in saline or a physiological buffer.

Therapeutic compositions comprising BPI protein product (including the peptide-based constructs or compositions of the invention) may be administered systemically or topically. Systemic routes of administration include oral, intravenous, intramuscular or subcutaneous injection (including into a depot for long-term release), intraocular and retrobulbar, intrathecal, intraperitoneal (e.g. by intraperitoneal lavage), intrapulmonary (using powdered drug, or an-aerosolized or nebulized drug solution), or transdermal. Topical routes include administration in the form of salves, ophthalmic drops, ear drops, or irrigation fluids (for, e.g., irrigation of wounds).

When given parenterally, BPI protein product compositions are generally injected in doses ranging from 1 µg/kg to 100 mg/kg per day, preferably at doses ranging from 0.1 mg/kg to 20 mg/kg per day. The treatment may continue by continuous infusion or intermittent injection or infusion, at the same, reduced or increased dose per day for, e.g., 1 to 3 days, and additionally as determined by the treating physician.

Those skilled in the art can readily optimize effective dosages and administration regimens for therapeutic compositions comprising BPI protein product (including the constructs or compositions of the present invention), as determined by good medical practice and the clinical condition of the individual subject.

The constructs or compositions of the invention may be used in any of the therapeutic uses for which BPI products are known to be effective, including those described above. The constructs are particularly useful in methods for binding and neutralizing exogenous heparin, methods for inhibiting endothelial cell proliferation, treating disorders associated with endothelial cell proliferation, methods for inhibiting angiogenesis, and treating disorders associated with or involving angiogenesis.

Exogenous heparin compounds are commonly administered during surgical procedures requiring anticoagulation, such as cardiopulmonary bypass, cardiac catheterization or angioplasty, and hemodialysis. Exogenous heparin compounds are also administered to patients at risk of or suffering from thrombosis, e.g. patients suffering from deep venous thrombosis, acute myocardial infarction, stroke, or pulmonary embolism.

Angiogenesis-associated disorders are disorders in which angiogenesis plays a role in the initiation or progression of disease. Angiogenesis is involved in a number of conditions, illustrated below, and inhibition of angiogenesis is expected to be effective for treating any of these conditions (including inhibiting progression of the disease and ameliorating signs and symptoms of the disease).

Use of the constructs of the invention in preparation of a medicament for any of these therapeutic uses is also contemplated.

Angiogenesis is of considerable importance in cancer conditions because new vessel production is required to support the rapid growth of cancer cells. Inhibition of angiogenesis thus may promote tumor regression in adult and pediatric oncology, including reducing growth of solid tumors/malignancies, locally advanced tumors, metastatic cancer, human soft tissue sarcomas, cancer metastases, including lymphatic metastases, blood cell malignancies, effusion lymphomas (body cavity based lymphomas), lung cancer, including small cell carcinoma, non-small cell cancers, breast cancer, including small cell carcinoma and ductal carcinoma, gastrointestinal cancers, including stomach cancer, colon cancer, colorectal cancer, polyps associated with colorectal neoplasia, pancreatic cancer, liver cancer, urological cancers, including bladder cancer, prostate cancer, malignancies of the female genital tract, including ovarian carcinoma, uterine endometrial cancers, and solid tumors in the ovarian follicle, kidney cancer, including renal cell carcinoma, brain cancer, including intrinsic brain tumors, neuroblastoma, astrocytic brain tumors, gliomas, metastatic tumor cell invasion in the central nervous system, bone cancers, including osteomas, skin cancers, including malignant melanoma, tumor progression of human skin keratinocytes, and squamous cell cancer, hemangiopericytoma, and Kaposi's sarcoma.

Angiogenesis also plays a role in chronic inflammation, including chronic pancreatitis, dermatosis associated with chronic inflammation, including psoriasis, cirrhosis, asthma, multiple sclerosis, arthritis, including rheumatoid arthritis, reactive arthritis and chronic inflammatory arthritis, autoimmune disorders, including vasculitis, glomerulonephritis, experimental allergic encephalomyelitis (EAE), lupus, myasthenia gravis, ulcerative colitis, Crohn's disease, inflammatory bowel disease, chronic inflammation associated with hemodialysis, granulocyte transfusion associated syndrome; rejection reactions after allograft and xenograft transplantation, including graft versus host disease; and other chronic inflammatory disorders.

Angiogenesis in the eye is involved in ocular neovascularization, proliferative retinopathy, retrolental fibraplasia, macular degeneration, neovascular glaucoma and diabetic ocular disease, in particular, diabetic iris neovascularization and retinopathy.

Coronary atheroma are highly vascularized by a fragile capillary network, and rupture of these newly formed capillaries when they are exposed to high intravascular pressures may lead to hemorrhage into atherosclerotic plaques and coronary occlusion. Inhibition of angiogenesis thus may reduce the growth of atherosclerotic plaques and may be useful in the treatment of atherosclerosis, ischemic heart disease, myocardial infarction, coronary heart disease, restenosis, particularly following balloon angiography, neointimal hyperplasia, disruption of intercellular junctions in vascular endothelium, hypertension, vessel injury, arterial ischemia, arterial stenosis, peripheral-vascular disease, stroke Angiogenesis also occurs during the female reproductive cycle and is involved in endometriosis, uterine fibroids, other conditions associated with dysfunctional vascular proliferation (including endometrial microvascular growth) during the female reproductive cycle.

Angiogenesis is also involved in abnormal vascular growth, including cerebral arteriovenous malformations (AVMs), angiofibronas, and hemangionas.

Concurrent administration of other therapeutic agents appropriate for the condition being treated (e.g., other agents that inhibit angiogenesis or cancer therapeutic agents if indicated) is also contemplated.

"Concurrent administration," or "co-administration," as used herein includes administration of the agents, in conjunction or combination, together, or before or after each other. The BPI protein product and second agent(s) may be administered by different routes. For example, the BPI protein product may be administered intravenously while the second agent(s) is(are) administered intravenously, intramuscularly, subcutaneously, orally or intraperitoneally. The BPI protein product and second agent(s) may be given sequentially in the same intravenous line or may be given in different intravenous lines. Alternatively, the BPI protein product may be administered in a special form for gastric delivery, while the second agent(s) is(are) administered, e.g., orally. The formulated BPI protein product and second agent(s) may be administered simultaneously or sequentially, as long as they are given in a manner sufficient to allow all agents to achieve effective concentrations at the site of action.

Other aspects and advantages of the present invention will be understood upon consideration of the following illustrative examples wherein Example 1 addresses preparation and purification of peptide-based constructs; Example 2 addresses in vitro activity of peptide-based constructs in an endothelial cell proliferation assay; Example 3 addresses in vivo testing of the anti-angiogenic activities of peptide-based constructs; Example 4 addresses the in vivo testing of peptide-based constructs in models of chronic inflammatory disease states; Example 5 addresses testing of peptide-based constructs in a malignant melanoma metastasis model; Example 6 addresses the in vitro testing of peptide-based constructs in oral absorption screening assays; Example 7 addresses the in vivo testing of peptide-based constructs for oral absorption; Example 8 addresses in vivo testing of peptide-based constructs for oral activity; and Example 9 addresses the in vitro and in vivo testing of peptide-based constructs in retinal neovascularization models.

EXAMPLE 1

Preparation and Purification of Peptide-Based Constructs

This example addresses the preparation and purification of peptide-based constructs according to the invention.

Peptide-based constructs may be prepared according to a variety of synthetic procedures. For example, BPI-derived peptides have been prepared by solid phase peptide synthesis as described in co-assigned U.S. patent application Ser. No. 08/183,222 and U.S. Pat. No. 5,733,872, according to the methods of Merrifield, 1963, *J. Am Chem. Soc.* 85: 2149 and Merrifield et al., 1966, *Anal. Chem.*, 38: 1905–1914 using an Applied Biosystems, Inc. Model 432 peptide synthesizer.

Alternatively, BPI-derived peptides have been synthesized on a larger scale using solid phase peptide synthesis on an Advanced Chemtech (ACT-Model 357 MPS) synthesizer utilizing a 1-Fluorenylmethyl-oxycarbonyl (Fmoc) protection strategy with a double coupling procedure employing N,N-diisopropylcarbodiimide (DIC)/1-hydroxybenzotriazole (HOBt) and 2-(1-H-benzotriazol-1-yl)-1,1,3,3,-tetramethyluronium hexa-fluorophosphate (HBTU)/HOBt/diisopropylethylamine (DIEA) as described in U.S. Pat. No. 5,858,974.

The solid support used in the synthesis of peptide-based constructs of the present invention was a polystyrene resin with 1% divinylbenzene (DVB) crosslinking and an 4-(2', 4'-dimethoxyphenyl-Fmoc-aminomethyl)-phenoxy (Fmoc-Rink amide) linker with a substitution rate of 0.56 mmoles/gram. A scale between 0.1 grams and 5 grams of starting resin may be used, and was generally 0.25 grams for the synthetic peptide-based constructs described herein.

For such syntheses, dimethylformamide (DMF) was the primary solvent with a 50/50 solution of piperidine/DMF used for Fmoc deprotection in three consecutive treatments of 1, 5, and 10 minutes, respectively. A double coupling procedure was used in each cycle with a 4:1 amino acid to peptide ratio used in each coupling. The amino acids were dissolved in a 0.5M HOBt solution in N-methylpyrrolidinone (NMP) at a concentration also of 0.5M. For the first coupling, an equimolar. (to amino acid)

amount of a 0.5M solution of diisopropylcarbodiimide (DIPCDI) in NMP was used and allowed to react for 45 minutes. The second coupling utilized an equimolar (to amino acid) volume of a 0.5M HBTU solution in DMF with an equal volume of a 1M DIEA solution in NMP (2:1, DIEA:amino acid) for a period of 30 minutes.

Upon completion of the synthesis, the resin was treated with MeOH, dried under reduced pressure, and then cleaved using a cocktail composed of trifluoroacetic acid (TFA):thioanisole:ethanedithiol(EDT):water, at a ratio of 36:2:1:1 (with the volume dependent on the amount of resin) for 2 hours (a minimum of 2 hours was used with an additional 30 minutes added for each arginine, but not exceeding 3 hours) with the first 15 minutes occurring in a wet ice bath. The solutions were then dissolved in a 10% TFA in water solution, washed 3 times with methyl t-butyl ether (MTBE) and lyophilized.

The amino termini of selected peptide-based constructs may be derivatized with acetic anhydride or other organic carboxylic acid after synthesis on solid phase using an N-terminal Fmoc protection strategy as described above. Subsequent to Fmoc removal with piperidine and prior to peptide cleavage with TFA, peptide on the resin could be derivatized with a 10-fold molar excess of acetic anhydride or 4-fold molar excess of other organic carboxylic acid with a 2-fold molar excess of diisopropylethylanine in dimethylformamide for one hour or a double coupling procedure employing N,N-diisopropylcarbodiimide (DIC) or CIPCDI/1-hydroxybenzotriazole (HOBt) and 2-(1-H-benzotriazol-1-yl)-1.1.3.3.-tetramethyluronium hexa-fluorophosphate (HBTU)/HOBt/diisopropylethylamine (DIEA) and one of a variety of building blocks could be used for derivatization. The peptide was then cleaved from the resin with the TFA cleavage cocktail as described above and purified as described below. Derivatization, including N-terminal acetylation, of the purified peptide was verified by mass spectrometry.

Yields of the peptide-based constructs described in Table I ranged from 9 to 26%. All HPLC purities were generally greater than 90% and mass was construed by mass spectrometry.

For purity analysis of each newly synthesized peptide-based construct, dilute solutions of lyophilized peptide-based constructs were prepared and analyzed on a Michrom Ultrafast Microprotein Analyzer equipped with a 150 mm×1 mm, 5$\mu$ particle, 300 Å pore C-8 Zorbax column. The column oven was set to 40° C., the flow rate was 100 $\mu$L/minute, and injection volumes were typically 5–10 $\mu$L. HPLC was performed using 5% acetonitrile/0.1% TFA in water as mobile phase A, and 80% acetonitrile/0.065% TFA as mobile phase B. The eluate was monitored spectrophotometrically at 214 nm. Percent purity was calculated from the peak area of the individual peptide constructs.

Selected constructs were purified by high performance liquid chromatography (HPLC), using a Waters Prep LC 2000 Preparative Chromatography System (Water Corp., Milford, Mass.) equipped with a Delta Pak C-18, 15 $\mu$m, 300 Å cartridge column consisting of a 40×10 mm guard cartridge and a 40×100 mm Prep Pak cartridge. The column was equilibrated in 25% buffer B, where A=5% acetonitrile/0.1% trifluoroacetic acid and B=80% acetonitrile/0.065% trifluoroacetic acid. Such peptide-based constructs were dissolved to ~20 mg/mL in buffer A and 200–800 mg were applied to the column through the LC pump operating at a flow rate of 8–17 mL/min. Bound material was eluted with a gradient of 25–35% buffer B/30 min applied at 8–17 mL/min. (Some constructs were purified with a gradient of 23–33% B/30 min.) The eluate was monitored at 220 and/or 280 and 300 nm with a Waters 490E Programmable Multiwavelength Detector. Fractions were collected and assayed for the construct of interest on an Ultrafast Micoprotein Analyzer (Michrom BioResources, Inc., Pleasanton, Calif.) equipped with a Zorbax C-8, 150×1 mm, 5 $\mu$m, 300 Å maintained at 40° C. Fractions containing the construct of interest at $\geq$90% purity were pooled and lyophilized to dryness. The purity of the recovered material was determined with analytical reverse-phase HPLC.

TABLE I

| Peptide Construct (SEQ ID NO:) | Sequence[a] | Molecular Weight |
|---|---|---|
| XMP.394 (1) | lys-leu-phe-arg-(D-naph-ala)-gln-ala-lys-(D-naph-ala)-lys-gly-ser-ile-lys-ile | 1910.4 |
| XMP.624 (2) | lys-leu-phe-arg-(D-naph-ala)-gln-ala-lys-(D-naph-ala)-lys-gly-ser-ile-lys | 1797.3 |
| XMP.625 (3) | lys-leu-phe-arg-(D-naph-ala)-gln-ala-lys-(D-naph-ala)-lys-gly-ser-ile | 1669.0 |
| XMP.626 (4) | lys-leu-phe-arg-(D-naph-ala)-gln-ala-lys-(D-naph-ala)-lys-gly-ser | 1555.8 |
| XMP.627 (5) | lys-leu-phe-arg-(D-naph-ala)-gln-ala-lys-(D-naph-ala)-lys-gly | 1468.7 |
| XMP.628 (6) | lys-leu-phe-arg-(D-naph-ala)-gln-ala-lys-(D-naph-ala)-lys | 1411.6 |
| XMP.629 (7) | lys-leu-phe-arg-(D-naph-ala)-gln-ala-lys-(D-naph-ala) | 1283.3 |
| XMP.630 (8) | lys-leu-phe-arg-(D-naph-ala)-gln-ala-lys | 1086.4 |
| XMP.656 (9) | lys-leu-phe-arg-(D-naph-ala)-gln-ala-lys-(D-naph-ala)-lys-gly-ile-lys-ile | 1823.5 |

TABLE I-continued

| Peptide Construct (SEQ ID NO:) | Sequence[a] | Molecular Weight |
|---|---|---|
| XMP.679 (10) | lys-leu-phe-lys-(D-naph-ala)-gln-ala-lys-(D-naph-ala)-lys-gly | 1440.2 |
| XMP.684 (11) | (D-biphenyl-ala)-lys-leu-phe-arg-(D-naph-ala)-gln-ala-lys | 1309.1 |

[a] by convention amino acid moieties written in lower case (e.g., lys) represent D-amino acid moieties and in upper case (e.g., LYS) represent L-amino acid moieties.

EXAMPLE 2

In Vitro Huvec Assay

This example addresses the activity of peptide-based constructs in an in vitro assay of endothelial cell proliferation.

Briefly, human umbilical vein endothelial cells (HUVEC) were cultured in EGM-2 medium (Clonetics Corp., San Diego, Calif.), harvested and plated onto a 96-well culture plate. After 24 hours of quiescence, the cells were co-cultured with various peptide-based constructs in the presence of growth factors for 72 hours to test their activity. Cell proliferation was quantitated by tritiated thymidine incorporation into DNA and was expressed in counts per minute (cpm).

Details of the experimental procedures were as follows: HUVEC cells were cultured in EGM-2 media from Clonetics Corp., a subsidiary of BioWhittaker, Inc., San Diego, Calif. [EGM-2 is Endothelial Cell Basal Medium-2 (EMB-2) supplemented with growth factors (hFGF-B, VEGF, IGF-1, hEGF) ascorbic acid, heparin, GA-1000 and 2% FBS), in T75 flasks until confluent (~4–7 days). Cells were harvested by trypsinizing the cells using 0.025% trypsin/EDTA for 5 minutes. To stop the reaction, 2–5% FBS was added. The cells were centrifuged and washed 3 times using Hank's Balanced Salt Solution (HBSS) or Dulbecco's Phosphate Buffered Saline D-PBS. The pellet was then resuspended in EBM-2 supplemented with 0.1% FBS and GA-1000 was used. The cells were counted and a cell suspension was prepared at $2 \times 10^5$ mL in EBM-2 with 0.1% FBS; cells were dispensed into a 96-well flat bottomed culture plate at 0.1 mL/well (total: ~20,000 cells/well in 0.1% FBS-EBM-2). Incubation continued at 37° C. in 5% $CO_2$ for 24 hours. The next day peptide-based constructs were prepared for testing in a 96 well plate. The supernatant was aspirated from the cell-well, replaced with EBM-2 or the testing reagent at 20 μL/well. Then, 180 μL/well of 1.12% FBS-GFS were added to make a final concentration of 1% FBS-GFS in EBM-2. This aspiration and addition was done well-by-well. $^3$H-thymidine (100 μCi/mL) was added at 10 μL/well (1 μCi/well, final). Incubation continued at 37° C., 5% $CO_2$ for 72 hours. To harvest the plate, the supernatant was aspirated off from the cell-well and then 75 μL-100 μL/well of 0.025% trypsin-EDTA was added. After incubation for 8–10 minutes at room temperature in the hood, the cells were checked and 100 μL/well of 2–5% FBS-PBS was added to stop the reaction. The plate was then harvested, dried and counted using an Inotech cell harvester (Inotech Biosystems, INB-384, Sample Processing and Filter Counting System, Lansing, Mich.).

Results of such HUVEC proliferation assays are shown in Table II. Tested in crude form (purity >73%), peptide-based constructs according to the invention inhibited HUVEC proliferation.

TABLE II

| Peptide Construct (SEQ ID NO:) | Moiety No. (Amino Acids) | Purity | $IC_{50}$ (μg/mL) |
|---|---|---|---|
| XMP.394 (1) | 15 | 95.2% | 4.3 ± 0.5 |
| XMP.624 (2) | 14 | 81.5% | 5.3 ± 0.3 |
| XMP.625 (3) | 13 | 95.4% | 3.1 ± 0.2 |
| XMP.626 (4) | 12 | 92.2% | 9.1 ± 0.7 |
| XMP.627 (5) | 11 | 88.4% | 5.8 ± 0.7 |
| XMP.628 (6) | 10 | 86.0% | 6.7 ± 0.7 |
| XMP.629 (7) | 9 | 86.4% | 5.4 ± 1.2 |
| XMP.630 (8) | 8 | 73.7% | >25 |
| XMP.656 (9) | 14 | 94.1% | ND |
| XMP.679 (10) | 11 | 92.8% | 6.3 ± 0.9 |
| XMP.684 (11) | 9 | 97.8% | 10 < x < 30 |

ND — Not Determined

Inhibitory activity with a 9-amino acid construct (XMP.629) was similar to that of the 15-amino acid parent construct (XMP.394).

EXAMPLE 3

In Vivo Matrigel® Angiogenesis Assay

This example addresses the activity of peptide-based constructs in an in vivo assay of angiogenesis using Matrigel®.

For these experiments, peptide-based constructs according to the invention were assayed for their ability to inhibit heparin-induced angiogenesis in vivo in mice. Basement membrane matrix (Matrigel®, Becton Dickinson Labware, Mountain View, Calif.) was thawed and maintained at 4° C. and angiogenic factors were added to the gel in the liquid state generally as described in Passaniti et al. 1992, *Lab. Invest.* 67: 519–528. Heparin sodium (Sigma, St. Louis, Mo.) was dissolved in sterile PBS to various concentrations ranging from 1,250–10,000 U/mL, and used in these experiments at 8,000 U/mL. Human recombinant basic fibroblast growth factor (bFGF; Sigma) was reconstituted into 1% BSA in PBS to 25 μg/ml. A volume of 2.5 μL dissolved heparin solution and 4.0 μL recombinant bFGF were added to 0.5 mL Matrigel® mixture per mouse injection. Peptide-based constructs were added to this Matrigel® mixture at varying concentrations ranging from 0.5 to 50 μL/mL (final concentration) in 10 μL/0.5 mL Matrigel® aliquot per experimental animal. Ten μL sterile PBS was substituted for peptide-based constructs in Matrigel® aliquots injected into control animals.

Female C57BL/6J mice (Jackson Laboratory, Bar Barbor, Me.) at 6–8 weeks of age (maintained under NIH guidelines) were injected subcutaneously down the dorsal midline with 0.5 mL aliquots of Matrigel® prepared as described above. Ten days after injection, the Matrigel® gels were excised and placed in Drabkin's reagent (Sigma). Total protein and hemoglobin content can be determined for the gels stored in Drabkin's reagent after mechanical homogenization of the gels. Hemoglobin concentration was measured using Sigma Procedure #525 and reagents supplied by Sigma (St. Louis, Mo.) to be used with this procedure. If desired, total protein levels are determined using a microplate assay that is commercially embodied in a kit (DC Protein Assay, Bio-Rad, Richmond, Calif.).

Gels to be used for histological staining are formalin-fixed immediately after excision from the animals rather than being placed in Drabkin's reagent. Formalin-fixed gels are embedded in Tissue-Tek O.C.T. compound (Miles, Inc., Elkhart, Ind.) for frozen sectioning. Slides of frozen sections are stained with hematoxylin and eosin (as described by Humason, 1979, *Animal Tissue Techniques*, $4^{th}$ Ed. W.H. Feeman & Co., San Francisco, Calif., Ch. 9, pp. 111–131). The effect of peptides are detected by microscopic examination of frozen stained sections for inhibition of angiogenesis relative to Matrigel® gel slices prepared without added peptides. The extent of angiogenesis inhibition is quantitated using the normalized amounts of hemoglobin found in BPI peptide-containing gel slices.

Results of Matrigel® assays are shown in Table III. Data are presented as the means of triplicate determinations of hemoglobin concentrations from the excised gel (ISEM) with ten mice per group.

TABLE III

| Peptide Construct (SEQ ID NO:) | % Inhibition | p-value |
| --- | --- | --- |
| XMP.394 (1) | 54.6 | 0.03 |
| XMP.624 (2) | ND | ND |
| XMP.624 (3) | 51.9 | 0.04 |
| XMP.626 (4) | ND | ND |
| XMP.627 (5) | 77.6 | 0.003 |
| XMP.628 (6) | ND | ND |
| XMP.629 (7) | 30.8 | 0.22 |
| XMP.630 (8) | 49.6 | 0.05 |

ND — Not Determined

Peptide-based constructs inhibited bFGF-induced angiogenesis. Matrigel® assay results corroborated HUVEC assay results described in Example 2.

EXAMPLE 4

Chronic Inflammatory Disease State Models: Collagen-Induced Arthritis or Reactive Arthritis This example addresses the in vivo activity of peptide-based constructs when they are administered for their effects in chronic inflammatory disease states such as arthritis.

For the collagen-induced arthritis model, arthritis is induced in mice by intradermal immunization of bovine Type II collagen at the base of the tail according to the method of Stuart et al., 1982, *J. Clin. Invest.* 69: 673–683. Generally, mice begin to develop arthritic symptoms at day 21 after collagen immunization. The arthritic scores of the treated mice are then evaluated in a blinded fashion over a period of 120 days for mice treated on each of days 21–25 with injection intravenously via the tail vein of peptide-based constructs prepared in accordance with Example 1, or of buffer as a control.

Specifically, bovine Type II collagen (Southern Biotechnology Associates, Inc., Birmingham Ala.) is administered via intradermal injection (0.1 mg/mouse) at the base of the tail on day 0 to groups of male mice (Mouse/DBA/1J), each weighing approximately 20–25 g. Peptide-based constructs are dissolved in a buffer comprised of 0.5M NaCl, 20 mM sodium acetate (pH 6.0) and diluted with PBS buffer for administration at various concentrations. PBS buffer alone (0.1 mL) is administered as a control.

The collagen-induced arthritis model is also used to evaluate the performance of peptides in comparison with protamine sulfate. Specifically, peptide-based constructs are dissolved in PBS as described above and administered at various concentrations. The other test materials are administered at the following dosages: protamine sulfate (Sigma Chemical Co., St. Louis, Mo.) (0.13 mg/mouse), thaumatin control protein (0.12 mg/mouse), and PBS buffer (0.1 mL). Groups of mice receive test or control materials through intravenous injection via the tail vein on each of days 28 through 32 post-injection with collagen.

For the reactive arthritis model, peptide-based constructs are administered to treat reactive arthritis in a *Yersinia enterocolitica* reactive arthritis model according to the method of Yong et al., 1988, *Microbial Pathogenesis* 4: 305–310. Specifically, peptide-based constructs are administered to DBA/2J mice which have previously been injected intravenously with Yersinia enterocolitica cWA 0:8 T2 (i.e., lacking the virulence plasmid according to Yong et al., supra) at a dosage of $4 \times 10^8$ bacteria calculated to induce a non-septic arthritis in the mice. Groups of mice each receive test or control materials through intravenous injection via the tail vein.

*Borrelia burgdorferi* is the pathogen responsible for Lyme Disease and associated arthritis and it possesses an LPS-like complex on its cell walls which is different from but structurally related to that of *E. coli*. The effect of administration of the peptide-based constructs on inhibition of *B. burgdoferi* LPS in a Limulus Amoebocyte Lysate (LAL) inhibition assay is determined. Specifically, an LAL assay is conducted measuring the effect of peptide-based constructs on *B. burgdorferi* LPS administered, for example, at 2.5 µg/mL and *E. coli* 0113 LPS administered, for example, at 2 ng/mL.

EXAMPLE 5

Malignant Melanoma Metastasis Model

This example addresses the activity of peptide-based constructs in an in vivo malignant melanoma metastasis model.

For these experiments, peptide-based constructs, protamine, or buffer controls are administered to test their efficacy in a mouse malignant melanoma metastasis model. Specifically, groups of C57BL/6J mice are inoculated with $10^5$ B16.F10 malignant melanoma cells via intravenous injection into the tail vein on day 0. Peptide-based constructs prepared in accordance with Example 1 in various concentrations are administered into the tail vein of test mice on days 1, 3, 6, 8, 10, 13, 15, 17, and 19. Protamine sulfate (0.13 mg/mouse) as a positive control, or PBS buffer (0.1 mL/mouse) as a negative control are similarly administered to additional groups of control mice. The animals are either sacrificed via cervical dislocation on day 20 for observation of lung tissues or observed for mortality until day 40. The lobes of each lung are perfused and inflated by injecting 3 mL water into the lung via the trachea. Superficial tumor nodules are then counted with the aid of a dissecting microscope and the number of tumors found per group analyzed for statistically significant differences. Such analyses identify those constructs with efficacy that significantly reduce the number of tumors and significantly prolong survival.

EXAMPLE 6

In Vitro Oral Absorption Screening

This example addresses the activity of peptide-based constructs in in vitro transport screening assays.

For these experiments, peptide-based constructs are screened for potential oral absorption in in vitro screening assays using MDCK and/or CACO-2 cells. Briefly, cultured monolayers of Madin-Derby canine kidney epithelial (MDCK) cells (ATCC Accession No. CCL-34) and/or CACO-2 (Human colon carcinoma) cells (Audus, K. L., et al., 1990, *Phar. Res.*, 7:435–451) are grown upon collagen-coated, permeable-filter supports (Becton Dickinson, Mountain View, Calif.). The cells are grown to confluency and allowed to differentiate (e.g., about 3 days for MDCK cells or about 21 days for CACO-2 cells). The integrity of the monolayers is determined by measuring the transepithelial resistance. The cells are incubated with a peptide-based construct on the apical side for 2.5 hours in MDCK or CACO-2 screening. The transepithelial transport of the construct is measured by quantitative HPLC analysis of the incubation media on the basolateral side of the cells (forward transport). Radiolabelled mannitol and/or cortisone are used as positive controls. In addition, the efflux of the construct is measured by quantitative HLPC analysis of the incubation media on the apical side of the cells. This follows incubation of the cells with construct on the basolateral side for 2.5 hours.

Details of the experimental procedures were as follows: MDCK or CACO-2 cells are grown to ~90% confluency in T75 tissue culture flasks in cell growth media (for MDCK cells, Minimum Essential Medium (Eagle's) GIBCO (Grand Island, N.Y.) #11095-080 or for CACO-2 cells, DMEM, GIBCO #11965-050, high glucose—500 mL; FBS 10% (Hyclone) heat treated—50 mL; L-Glutamine (200 mM) GIBCO #25030-016—5 mL; for CACO-2 cells, Non-essential amino acids, GEBCO #11140-050 (200 mM, 100×)—5.5 mL; and Penicillin/Streptomycin (100 µg/mL) GEBCO #15140-015—5 mL, that has been filtered and stored at 4° C.). The cells are trypsinized (~20 minutes for MDCK cells for passaging due to their tight adherence) and seeded on 24.5 mm transwells (Transwell-COL, #3245, Corning CoStar Corp., Cambridge, Mass.) at a concentration of ~3×10$^6$ MDCK cells/well or ~3×10$^5$ CACO-2 cells/well. For the MDCK cells, media is changed one day post seeding and the MDCK cells are allowed to grow for an additional 2 days. For the CACO-2 cells, media is changed every 2 days post seeding and the CACO-2 cells are allowed to grow for a total of up to 21 days.

Following the days post seeding, the cells are ready for transport experiments. The cells are fed fresh media 2 hours before starting the transport experiment. The cells are then washed with transport media (TM: Hank's Balanced Salt Solution (HBSS) GIBCO #14025-027, with no phenol red; 10 mM HEPES (from 1 M HEPES) GIBCO #15630-015, pH balanced with NaOH to 7.4) and placed in new 6 well plates. Donor solutions of peptide-based constructs for assay are prepared in 1.5 mL TM at a concentration of ~100 µg/mL. For forward transport studies, these 1.5 mL construct solutions are added to the apical chamber of the transwells. Approximately 2.6 mL of acceptor solution (TM only, no construct) is added to the basolateral chamber. For efflux studies, the donor solution with construct is added to the basolateral chamber and acceptor solution (TM only, no construct) is added to the apical chamber. Each construct is assayed at least in triplicate.

The transwells are returned to the 37° C. tissue culture incubator for 2.5 hours. At the end of 2.5 hours the apical and basolateral solutions are separately freeze dried (lyophilized) in high vacuum in 15 mL conical tubes. The samples are then resuspended in 200 µL HPLC buffer A (5% acetonitrile: 95% water: 0.1% tetrafluoroacetic acid (TFA)) and 50 µL of the resuspended sample is used for HPLC analysis.

Apical control wells containing 1.5 mL TM with tritiated mannitol ($^3$H-mannitol, 1 µCi/mL; Dupont NEN Research Products, #NET-101, Boston, Mass.) are analyzed separately for counts per minute (cpm) of tritium to test the integrity of the MDCK cell monolayers.

Forward transport is calculated as the percentage of peptide-based construct in the basolateral chamber (determined by the area under the HPLC peak) to the initial concentration of the apical solution (initial donor concentration of ~100 µg/mL). For efflux experiments, the reverse calculation is made (percentage of peptide-based construct in the apical chamber to the initial construct concentration in the basolateral solution). Such intestinal absorption screening identifies constructs that are potential orally available compounds.

EXAMPLE 7

In Vivo Oral Absorption Screening

This example addresses the activity of peptide-based constructs for oral absorption in an in vivo screening assay in which constructs are administered by oral gavage to mice.

Briefly, serum concentrations of the constructs are measured at various time intervals after administration by HPLC. For example, constructs may be administered to mice at various dosages (e.g., 10 mg/kg body weight or 20 mg/kg body weight) and serum peptide concentrations are measured at various time intervals (e.g., 1 hours, 4 hours, and/or 24 hours) after administration to the mice. HPLC analysis identifies constructs that are absorbed after oral administration. Such constructs showing increased oral availability may achieve therapeutically effective serum concentrations after oral administration.

EXAMPLE 8

Oral Activity

This example addresses the activity of peptide-based constructs for activity upon oral administration (oral activity) in an in vivo animal model.

Animal models useful for testing oral activity include those described in Examples 4 and 5 above. Treatment is initiated by oral gavage (~400 µl) of either 0.5% dextrose, or the test peptide-based construct in 0.5% dextrose at various dosage levels (e.g., 10 mg/kg or 20 mg/kg according to the dosing regimen). Daily monitoring for efficacy is performed. The animals treated with orally active peptide-based constructs show improvement compared with the dextrose-treated controls.

EXAMPLE 9

Retinal Neovascularization Model

This example addresses the in vivo activity of peptide-based constructs when they are administered for their effects in a retinal neovascularization model.

In these experiments, peptide-based constructs are tested for their activity on the action of VEGF, bFGF, IGF-1 and conditioned media (hypoxia and hyperglycemia) on the in vitro growth and migration of retinal pigmented epithelial cells (RPE), retinal microvessel pericytes, and retinal endothelial cells. Effects are evaluated on gene expression under hypoxic or hypoglycemic conditions. In additional experiments, the effects of such constructs are characterized in vivo on the neovascular responses to hyperoxia in the retina of the neonatal mouse.

For the in vitro culture experiments, retinal microvessel pericytes, retinal endothelial cells, and retinal pigmented epithelial cells (RPE) are cultured from bovine retina. Dose responses and time course for growth and migration as stimulated by VEGF, bFGF, and IGF-1 are performed. In addition, conditioned media collected from cultured RPE, pericytes, and endothelial cells exposed to hypoxic or hyperglycemic conditions is collected in serum free media. When the dose responses of these growth factors and conditioned media are determined, the effect of peptide-based constructs independently, and in combination with the growth factors described above, are tested in growth and migration assays.

For the in vivo experiments, studies are performed to evaluate the effect of peptide-based constructs on retinal neovascularization. Neonatal mice are exposed to 100% $O_2$ for an extended period of time and then removed. This increased oxygenation delays development of the retinal vasculature such that, when they are returned to room air, the retinas are severely hypoxic and release of many cytokines occur, including VEGF, bFGF, IGF-1, and others. Retinal neovascularization occurs in 100% of animals. The severity of retinal neovascularization is quantitated by counting endothelial cell nuclei internal to the internal limiting membrane in retinal sections. VEGF and KDR expressions are evaluated by in situ hybridization, Northern and Western blot analysis. Tyrosine phosphorylation pattern of the whole retina is also evaluated by Western blot analysis. Peptide-based constructs are identified that inhibit or reduce retinal neovascularization.

Other peptide-based constructs are described in concurrently, filed U.S. application Ser. No. 09/344,541, now U.S. Pat. No. 6,355,616 ["Derivative Compounds",] and U.S. application Ser. No. 09/344,827, now U.S. Pat. No. 6,423,825 ["Therapeutic Derivative Compounds",] and are hereby incorporated by reference in their entirety. All U.S. patents, U.S. patent applications, International PCT Publications and references cited herein are hereby incorporated by reference in their entirety. Numerous modifications and variations of the above-described invention are expected to occur to those of skill in the art. Accordingly, only such limitations as appear in the appended claims should be placed thereon.

What is claimed is:

1. A pharmaceutical composition comprising a peptide-based construct of 8–14 amino acid moieties in length having heparin binding, heparin neutralizing, endothelial cell proliferation inhibiting, antiangiogenic LPS binding, LPS neutralization, or antimicrobial properties comprising:

a sequence having the formula:

$$\alpha\text{-}\chi\text{-}\chi\text{-}\alpha\text{-}\chi\text{-}\beta\text{-}\chi\text{-}\alpha\text{-}R$$

wherein, $\alpha$ is a hydrophilic basic amino acid moiety selected from the group consisting of lysine, arginine, histidine, ornithine, diamiriobutyric acid, citrulline, and para-amino phenylalanine;

$\beta$ is a hydrophilic neutral amino acid moiety selected from the group consisting of asparagine, glutamine, serine, threonine, tyrosine, hydroxyproline, and 7-hydroxy-tetrahydroisoquinoline carboxylic acid;

$\chi$ is a hydrophobic amino acid moiety selected from the group consisting of alanihe, naphthylalanine, biphenylalanine, valine, leucine, isoleucine, proline, hydroxyproline, phenylalanine, tryptophan, methionirie, glycine, cyclohexylalanine, amino-isobutyric acid, norvaline, norleucine, tert-leucine, tetrahydroisoquinoline carboxylic acid, pipecolic acid, phenylglycine, homophenylalanine, cyclohexylglycine, dehydroleucine, 2,2-diethylglycine, 1-amino-1-cyclopentane carboxylic acid, 1-amino-1-cyclohexane carboxylic acid, amino-benzoic acid, amino-naphthyl carbbxylic acid, $\gamma$-amino butyric acid, beta-alanine, difluorophenylalanine, fluorophenylalanine, nipecotic acid, aminobutyric acid, thienyl-alanine, and t-butyl-glycine; and R is an amino acid moiety selected from the group consisting of $-\chi$, $-\chi-\alpha$, $-\chi-\alpha-\chi$, $\chi-\alpha-\chi-\beta$, $-\chi-\alpha-\chi-\beta-\chi$, $-\chi-\alpha-\chi-\beta-\chi-\alpha$, $-\chi-\beta-\chi-\chi-\beta-\chi$, $-NH_2$, $-\chi-NH_2$, $-\chi-\alpha-NH_2$, $-\chi-\alpha-\chi-NH_2$, $-\chi-\alpha-\chi-\beta-NH_2$, $-\chi-\alpha-\chi-\beta-\chi-NH_2$, $-\chi-\alpha-\chi-\beta-\chi-\alpha-NH_2$, and $-\chi-\beta-\chi-\chi-\beta-\chi-NH_2$, and a pharmaceutically acceptable diluent, adjuvant, or carrier.

2. A pharmaceutical composition comprising a composition of 8–14 amino acid moieties consecutively linked by peptide ttonds, said composition having heparin binding properties and comprising a sequence of the formula:

$$KLFR(naph\text{-}A)QAR_1$$

wherein $R_1$ is seleted from the group consisting of K (SEK ID NO: 8), K(naph-A) (SEQ ID NO: 7), K(naph-A)K (SEQ ID NO: 6), K(naph-A)KG (SEQ ID NO: 5), K(naph-A)KGS (SEQ ID NO: 4), K(naph-A)KGSI (SEQ ID NO: 3), and K(naph-A)KGSIK (SEQ ID NO: 2); and wherein the carboxyl terminal group is amidated or nonamidated, and conservative substitution variants thereof having hepanin binding properties, and a pharmaceutically acceptable diluent, adjuvant, or carrier.

3. The pharmaceutical composition of claim 2 wherein the composition comprises at least one conservative substitution.

4. The pharmaceutical compositioni of claim 1 or 2 wherein the peptide-based construct or composition has heparin neutralizing properties.

5. The pharmaceutical composition, of claim 1 or 2 wherein the peptide-based construct or composition has endothelial cell proliferation inhibiting properties.

6. The pharmaceutical composition of claim 1 or 2 wherein the peptide-based construct or composition has anti-angiogenic properties.

7. The pharmaceutical composition of claim 1 or 2 comprising a peptide-based construct or composition wherein the first two amino-terminal amino acid moieties are D-amino acid moieties and the last two carboxy-terminal amino acid moieties are D-amino acid moieties.

8. A method of neutralizing heparin in a mammal that has been administered an exogenous heparin compound comprising the step of administering to said mammal an amount of the pharmaceutical composition of claim 1 or 2 effective to neutralize the anticoagulant effect of the exogenous heparin compound.

9. The method of claim 8 wherein the clotting time of said mammal is returned to normal.

10. A method of inhibiting endothelial cell proliferation in a mammal in need thereof comprising the step of administering to said mammal an amount of the pharmaceutical composition of claim 1 or 2 effective, to inhibit endothelial cell proliferation.

11. A method of inhibiting angiogenesis in a mammal in need thereof comprising the step of administering to said mammal an amount of the pharmaceutical composition of claim 1 or 2 effective to inhibit angiogenesis.

12. The method of claim 11 wherein said angiogenesis is in the eye.

13. A method of treating a mammal suffering from a disorder involving angiogenesis comprising the step of administering to said mammal an amount of the pharmaceutical composition of claim 1 or 2 effective to inhibit angiogenesis.

14. The method of claim 13 wherein said disorder involving angiogenesis is a chronic inflammatory disease.

15. The method of claim 14 wherein said chronic inflammatory disease is rheumatoid or reactive arthritis.

16. The method of claim 13 wherein said disorder involving angiogenesis is proliferation or metastasis of tumor cells.

* * * * *

SEQUENCE LISTING

```
<160> NUMBER OF SEQ ID NOS: 13

<210> SEQ ID NO 1
<211> LENGTH: 15
<212> TYPE: PRT
<213> ORGANISM: derived from human
<220> FEATURE:
<223> OTHER INFORMATION: XMP.394
<220> FEATURE:
<221> NAME/KEY: SITE
<222> LOCATION: (5)
<223> OTHER INFORMATION: /label=Substituted-Ala note=position 5 is
      naph-ala
<220> FEATURE:
<221> NAME/KEY: SITE
<222> LOCATION: (9)
<223> OTHER INFORMATION: /label=Substituted-Ala note=position 9 is
      naph-ala
<220> FEATURE:
<221> NAME/KEY: SITE
<222> LOCATION: (1)..(15)
<223> OTHER INFORMATION: /Label=D Amino Acids/note=Positions 1-15 are
      D-amino acids
<220> FEATURE:
<221> NAME/KEY: SITE
<222> LOCATION: (15)
<223> OTHER INFORMATION: AMIDATION /label=Amidation note=The C-terminus
      is Amidated

<400> SEQUENCE: 1

Lys Leu Phe Arg Ala Gln Ala Lys Ala Lys Gly Ser Ile Lys Ile
  1               5                  10                  15

<210> SEQ ID NO 2
<211> LENGTH: 14
<212> TYPE: PRT
<213> ORGANISM: derived from human
<220> FEATURE:
<223> OTHER INFORMATION: XMP.624
```

```
<220> FEATURE:
<221> NAME/KEY: SITE
<222> LOCATION: (5)
<223> OTHER INFORMATION: /label=substituted-Ala note=position 5 is
      naph-ala
<220> FEATURE:
<221> NAME/KEY: SITE
<222> LOCATION: (9)
<223> OTHER INFORMATION: /label=substituted-Ala note=position 9 is
      naph-ala
<220> FEATURE:
<221> NAME/KEY: SITE
<222> LOCATION: (1)..(14)
<223> OTHER INFORMATION: /Label=D Amino Acids/note=Positions 1-14 are
      D-amino acids
<220> FEATURE:
<221> NAME/KEY: SITE
<222> LOCATION: (14)
<223> OTHER INFORMATION: AMIDATION /label=Amidation note=The C=terminus
      is Amidated

<400> SEQUENCE: 2

Lys Leu Phe Arg Ala Gln Ala Lys Ala Lys Gly Ser Ile Lys
  1               5                  10

<210> SEQ ID NO 3
<211> LENGTH: 13
<212> TYPE: PRT
<213> ORGANISM: derived from human
<220> FEATURE:
<223> OTHER INFORMATION: XMP.625
<220> FEATURE:
<221> NAME/KEY: SITE
<222> LOCATION: (5)
<223> OTHER INFORMATION: /label=Substituted-Ala note=position 5 is
      naph-ala
<220> FEATURE:
<221> NAME/KEY: SITE
<222> LOCATION: (9)
<223> OTHER INFORMATION: /label=substituted-Ala note=position 9 is
      naph-ala
<220> FEATURE:
<221> NAME/KEY: SITE
<222> LOCATION: (1)..(13)
<223> OTHER INFORMATION: /Label=D Amino Acid/note=Positions 1-13 are
      D-amino acids
<220> FEATURE:
<221> NAME/KEY: SITE
<222> LOCATION: (13)
<223> OTHER INFORMATION: AMIDATION /label-=Amidation note=The C-terminus
      is Amidated

<400> SEQUENCE: 3

Lys Leu Phe Arg Ala Gln Ala Lys Ala Lys Gly Ser Ile
  1               5                  10

<210> SEQ ID NO 4
<211> LENGTH: 12
<212> TYPE: PRT
<213> ORGANISM: derived from human
<220> FEATURE:
<223> OTHER INFORMATION: XMP.626
<220> FEATURE:
<221> NAME/KEY: SITE
<222> LOCATION: (5)
<223> OTHER INFORMATION: /label-Substituted-Ala note=position 5 is
      naph-ala
<220> FEATURE:
<221> NAME/KEY: SITE
<222> LOCATION: (9)
<223> OTHER INFORMATION: /label-Substituted-Ala note=position 9 is
      naph-ala
<220> FEATURE:
<221> NAME/KEY: SITE
<222> LOCATION: (1)..(12)
```

```
<223> OTHER INFORMATION: /Label=D Amino Acids/note=Positions 1-12 are
      D-amino acids
<220> FEATURE:
<221> NAME/KEY: SITE
<222> LOCATION: (12)
<223> OTHER INFORMATION: AMIDATION /label=Amidation note=The C-terminus
      is Amidated

<400> SEQUENCE: 4

Lys Leu Phe Arg Ala Gln Ala Lys Ala Lys Gly Ser
 1               5                  10

<210> SEQ ID NO 5
<211> LENGTH: 11
<212> TYPE: PRT
<213> ORGANISM: derived from human
<220> FEATURE:
<223> OTHER INFORMATION: XMP.627
<220> FEATURE:
<221> NAME/KEY: SITE
<222> LOCATION: (5)
<223> OTHER INFORMATION: /label=Substituted Ala note=position 5 is
      naph-ala
<220> FEATURE:
<221> NAME/KEY: SITE
<222> LOCATION: (9)
<223> OTHER INFORMATION: /label=Substituted Ala note=position 9 is
      naph-ala
<220> FEATURE:
<221> NAME/KEY: SITE
<222> LOCATION: (1)..(11)
<223> OTHER INFORMATION: /Label=D Amino Acids/note=Positions 1-11 are
      D-amino acids
<220> FEATURE:
<221> NAME/KEY: SITE
<222> LOCATION: (11)
<223> OTHER INFORMATION: AMIDATION /label=Amidation note=The C-terminus
      is Amidated

<400> SEQUENCE: 5

Lys Leu Phe Arg Ala Gln Ala Lys Ala Lys Gly
 1               5                  10

<210> SEQ ID NO 6
<211> LENGTH: 10
<212> TYPE: PRT
<213> ORGANISM: derived from human
<220> FEATURE:
<223> OTHER INFORMATION: XMP.628
<220> FEATURE:
<221> NAME/KEY: SITE
<222> LOCATION: (5)
<223> OTHER INFORMATION: /label=Substituted-Ala note=position 5 is
      naph-ala
<220> FEATURE:
<221> NAME/KEY: SITE
<222> LOCATION: (6)
<223> OTHER INFORMATION: /label-Substituted-Ala note=position 9 is
      naph-ala
<220> FEATURE:
<221> NAME/KEY: SITE
<222> LOCATION: (1)..(10)
<223> OTHER INFORMATION: /Label=D Amino Acid/note=Positions 1-10 are
      D-amino acids
<220> FEATURE:
<221> NAME/KEY: SITE
<222> LOCATION: (10)
<223> OTHER INFORMATION: AMIDATION /label=Amidation note=The C-terminus
      is Amidated

<400> SEQUENCE: 6

Lys Leu Phe Arg Ala Gln Ala Lys Ala Lys
 1               5                  10
```

```
<210> SEQ ID NO 7
<211> LENGTH: 9
<212> TYPE: PRT
<213> ORGANISM: derived from human
<220> FEATURE:
<223> OTHER INFORMATION: XMP.629
<220> FEATURE:
<221> NAME/KEY: SITE
<222> LOCATION: (5)
<223> OTHER INFORMATION: /label=Substituted-Ala note=position 5 is
      naph-ala
<220> FEATURE:
<221> NAME/KEY: SITE
<222> LOCATION: (9)
<223> OTHER INFORMATION: /label=Substituted-Ala note=position 9 is
      naph-ala
<220> FEATURE:
<221> NAME/KEY: SITE
<222> LOCATION: (1)..(9)
<223> OTHER INFORMATION: /Label=D Amino Acids/note=Positions 1-9 are
      D-amino acids
<220> FEATURE:
<221> NAME/KEY: SITE
<222> LOCATION: (9)
<223> OTHER INFORMATION: AMIDATION /label=Amidation note=The C-terminus
      is Amidated

<400> SEQUENCE: 7

Lys Leu Phe Arg Ala Gln Ala Lys Ala
 1               5

<210> SEQ ID NO 8
<211> LENGTH: 8
<212> TYPE: PRT
<213> ORGANISM: derived from human
<220> FEATURE:
<223> OTHER INFORMATION: XMP.630
<220> FEATURE:
<221> NAME/KEY: SITE
<222> LOCATION: (5)
<223> OTHER INFORMATION: /label=Substituted-Ala note=position 5 is
      naph-ala
<220> FEATURE:
<221> NAME/KEY: SITE
<222> LOCATION: (1)..(8)
<223> OTHER INFORMATION: /Label=D Amino Acids/note=Positions 1-8 are
      D-amino acids
<220> FEATURE:
<221> NAME/KEY: SITE
<222> LOCATION: (8)
<223> OTHER INFORMATION: AMIDATION /label=Amidation note=The C-terminus
      is Amidated

<400> SEQUENCE: 8

Lys Leu Phe Arg Ala Gln Ala Lys
 1               5

<210> SEQ ID NO 9
<211> LENGTH: 14
<212> TYPE: PRT
<213> ORGANISM: derived from human
<220> FEATURE:
<223> OTHER INFORMATION: XMP.656
<220> FEATURE:
<221> NAME/KEY: SITE
<222> LOCATION: (5)
<223> OTHER INFORMATION: /label=Substituted-Ala note=position 5 is
      naph-ala
<220> FEATURE:
<221> NAME/KEY: SITE
<222> LOCATION: (9)
<223> OTHER INFORMATION: /label=Substituted-Ala note=position 9 is
      naph-ala
```

```
<220> FEATURE:
<221> NAME/KEY: SITE
<222> LOCATION: (1)..(14)
<223> OTHER INFORMATION: /Label=D Amino Acids/note=Positions 1-14 are
      D-amino acids
<220> FEATURE:
<221> NAME/KEY: SITE
<222> LOCATION: (14)
<223> OTHER INFORMATION: AMIDATION /label=Amidation note=The C-terminus
      is Amidated

<400> SEQUENCE: 9

Lys Leu Phe Arg Ala Gln Ala Lys Ala Lys Gly Ile Lys Ile
 1               5                  10

<210> SEQ ID NO 10
<211> LENGTH: 11
<212> TYPE: PRT
<213> ORGANISM: derived from human
<220> FEATURE:
<223> OTHER INFORMATION: XMP.679
<220> FEATURE:
<221> NAME/KEY: SITE
<222> LOCATION: (5)
<223> OTHER INFORMATION: /label=Substituted-Ala note=position 5 is
      naph-ala
<220> FEATURE:
<221> NAME/KEY: SITE
<222> LOCATION: (9)
<223> OTHER INFORMATION: /label=Substituted-Ala note=position 9 is
      naph-ala
<220> FEATURE:
<221> NAME/KEY: SITE
<222> LOCATION: (1)..(11)
<223> OTHER INFORMATION: /Label=D Amino Acids/note=Positions 1-11 are
      D-Amino Acids
<220> FEATURE:
<221> NAME/KEY: SITE
<222> LOCATION: (11)
<223> OTHER INFORMATION: AMIDATION /label=Amidation note=The C-terminus
      is Amidated

<400> SEQUENCE: 10

Lys Leu Phe Lys Ala Gln Ala Lys Ala Lys Gly
 1               5                  10

<210> SEQ ID NO 11
<211> LENGTH: 9
<212> TYPE: PRT
<213> ORGANISM: derived from human
<220> FEATURE:
<223> OTHER INFORMATION: XMP.684
<220> FEATURE:
<221> NAME/KEY: SITE
<222> LOCATION: (1)
<223> OTHER INFORMATION: /label=Substituted Ala note=position 1 is
      biphenyl-ala
<220> FEATURE:
<221> NAME/KEY: SITE
<222> LOCATION: (6)
<223> OTHER INFORMATION: /label=Substituted Ala note=position 6 is
      naph-ala
<220> FEATURE:
<221> NAME/KEY: SITE
<222> LOCATION: (1)..(9)
<223> OTHER INFORMATION: /Label-D Amino Acids/note=Positions 1-9 are
      D-amino acids
<220> FEATURE:
<221> NAME/KEY: SITE
<222> LOCATION: (9)
<223> OTHER INFORMATION: AMIDATION /label=Amidation note=The C-terminus
      is Amidated
```

```
<400> SEQUENCE: 11

Ala Lys Leu Phe Arg Ala Gln Ala Lys
 1               5

<210> SEQ ID NO 12
<211> LENGTH: 1813
<212> TYPE: DNA
<213> ORGANISM: human
<220> FEATURE:
<221> NAME/KEY: CDS
<222> LOCATION: (31)..(1491)
<220> FEATURE:
<221> NAME/KEY: mat_peptide
<222> LOCATION: (124)..(1491)
<220> FEATURE:
<223> OTHER INFORMATION: rBPI

<400> SEQUENCE: 12
```

| | |
|---|---|
| caggccttga ggttttggca gctctggagg atg aga gag aac atg gcc agg ggc<br>                                                   Met Arg Glu Asn Met Ala Arg Gly<br>                                                       -30                    -25 | 54 |
| cct tgc aac gcg ccg aga tgg gtg tcc ctg atg gtg ctc gtc gcc ata<br>Pro Cys Asn Ala Pro Arg Trp Val Ser Leu Met Val Leu Val Ala Ile<br>        -20                      -15                      -10 | 102 |
| ggc acc gcc gtg aca gcg gcc gtc aac cct ggc gtg gtg gtc agg atc<br>Gly Thr Ala Val Thr Ala Ala Val Asn Pro Gly Val Val Val Arg Ile<br>     -5                  -1  1                  5 | 150 |
| tcc cag aag ggc ctg gac tac gcc agc cag cag ggg acg gcc gct ctg<br>Ser Gln Lys Gly Leu Asp Tyr Ala Ser Gln Gln Gly Thr Ala Ala Leu<br> 10                   15                  20                  25 | 198 |
| cag aag gag ctg aag agg atc aag att cct gac tac tca gac agc ttt<br>Gln Lys Glu Leu Lys Arg Ile Lys Ile Pro Asp Tyr Ser Asp Ser Phe<br>               30                  35                  40 | 246 |
| aag atc aag cat ctt ggg aag ggg cat tat agc ttc tac agc atg gac<br>Lys Ile Lys His Leu Gly Lys Gly His Tyr Ser Phe Tyr Ser Met Asp<br>           45                  50                  55 | 294 |
| atc cgt gaa ttc cag ctt ccc agt tcc cag ata agc atg gtg ccc aat<br>Ile Arg Glu Phe Gln Leu Pro Ser Ser Gln Ile Ser Met Val Pro Asn<br>        60                    65                  70 | 342 |
| gtg ggc ctt aag ttc tcc atc agc aac gcc aat atc aag atc agc ggg<br>Val Gly Leu Lys Phe Ser Ile Ser Asn Ala Asn Ile Lys Ile Ser Gly<br> 75                   80                  85 | 390 |
| aaa tgg aag gca caa aag aga ttc tta aaa atg agc ggc aat ttt gac<br>Lys Trp Lys Ala Gln Lys Arg Phe Leu Lys Met Ser Gly Asn Phe Asp<br> 90                   95               100             105 | 438 |
| ctg agc ata gaa ggc atg tcc att tcg gct gat ctg aag ctg ggc agt<br>Leu Ser Ile Glu Gly Met Ser Ile Ser Ala Asp Leu Lys Leu Gly Ser<br>               110                115               120 | 486 |
| aac ccc acg tca ggc aag ccc acc atc acc tgc tcc agc tgc agc agc<br>Asn Pro Thr Ser Gly Lys Pro Thr Ile Thr Cys Ser Ser Cys Ser Ser<br>           125                   130               135 | 534 |
| cac atc aac agt gtc cac gtg cac atc tca aag agc aaa gtc ggg tgg<br>His Ile Asn Ser Val His Val His Ile Ser Lys Ser Lys Val Gly Trp<br>         140                   145               150 | 582 |
| ctg atc caa ctc ttc cac aaa aaa att gag tct gcg ctt cga aac aag<br>Leu Ile Gln Leu Phe His Lys Lys Ile Glu Ser Ala Leu Arg Asn Lys<br>     155                 160               165 | 630 |
| atg aac agc cag gtc tgc gag aaa gtg acc aat tct gta tcc tcc aag<br>Met Asn Ser Gln Val Cys Glu Lys Val Thr Asn Ser Val Ser Ser Lys<br>170               175               180               185 | 678 |

-continued

| | | |
|---|---|---|
| ctg caa cct tat ttc cag act ctg cca gta atg acc aaa ata gat tct<br>Leu Gln Pro Tyr Phe Gln Thr Leu Pro Val Met Thr Lys Ile Asp Ser<br>190                   195                 200 | | 726 |
| gtg gct gga atc aac tat ggt ctg gtg gca cct cca gca acc acg gct<br>Val Ala Gly Ile Asn Tyr Gly Leu Val Ala Pro Pro Ala Thr Thr Ala<br>205                   210                  215 | | 774 |
| gag acc ctg gat gta cag atg aag ggg gag ttt tac agt gag aac cac<br>Glu Thr Leu Asp Val Gln Met Lys Gly Glu Phe Tyr Ser Glu Asn His<br>220                   225                 230 | | 822 |
| cac aat cca cct ccc ttt gct cca cca gtg atg gag ttt ccc gct gcc<br>His Asn Pro Pro Pro Phe Ala Pro Pro Val Met Glu Phe Pro Ala Ala<br>235                   240                 245 | | 870 |
| cat gac cgc atg gta tac ctg ggc ctc tca gac tac ttc ttc aac aca<br>His Asp Arg Met Val Tyr Leu Gly Leu Ser Asp Tyr Phe Phe Asn Thr<br>250                   255                 260                265 | | 918 |
| gcc ggg ctt gta tac caa gag gct ggg gtc ttg aag atg acc ctt aga<br>Ala Gly Leu Val Tyr Gln Glu Ala Gly Val Leu Lys Met Thr Leu Arg<br>270                   275                 280 | | 966 |
| gat gac atg att cca aag gag tcc aaa ttt cga ctg aca acc aag ttc<br>Asp Asp Met Ile Pro Lys Glu Ser Lys Phe Arg Leu Thr Thr Lys Phe<br>285                   290                 295 | | 1014 |
| ttt gga acc ttc cta cct gag gtg gcc aag aag ttt ccc aac atg aag<br>Phe Gly Thr Phe Leu Pro Glu Val Ala Lys Lys Phe Pro Asn Met Lys<br>300                   305                 310 | | 1062 |
| ata cag atc cat gtc tca gcc tcc acc ccg cca cac ctg tct gtg cag<br>Ile Gln Ile His Val Ser Ala Ser Thr Pro Pro His Leu Ser Val Gln<br>315                   320                 325 | | 1110 |
| ccc acc ggc ctt acc ttc tac cct gcc gtg gat gtc cag gcc ttt gcc<br>Pro Thr Gly Leu Thr Phe Tyr Pro Ala Val Asp Val Gln Ala Phe Ala<br>330                   335                 340                345 | | 1158 |
| gtc ctc ccc aac tcc tcc ctg gct tcc ctc ttc ctg att ggc atg cac<br>Val Leu Pro Asn Ser Ser Leu Ala Ser Leu Phe Leu Ile Gly Met His<br>350                   355                 360 | | 1206 |
| aca act ggt tcc atg gag gtc agc gcc gag tcc aac agg ctt gtt gga<br>Thr Thr Gly Ser Met Glu Val Ser Ala Glu Ser Asn Arg Leu Val Gly<br>365                   370                 375 | | 1254 |
| gag ctc aag ctg gat agg ctg ctc ctg gaa ctg aag cac tca aat att<br>Glu Leu Lys Leu Asp Arg Leu Leu Leu Glu Leu Lys His Ser Asn Ile<br>380                   385                 390 | | 1302 |
| ggc ccc ttc ccg gtt gaa ttg ctg cag gat atc atg aac tac att gta<br>Gly Pro Phe Pro Val Glu Leu Leu Gln Asp Ile Met Asn Tyr Ile Val<br>395                   400                 405 | | 1350 |
| ccc att ctt gtg ctg ccc agg gtt aac gag aaa cta cag aaa ggc ttc<br>Pro Ile Leu Val Leu Pro Arg Val Asn Glu Lys Leu Gln Lys Gly Phe<br>410                   415                 420                425 | | 1398 |
| cct ctc ccg acg ccg gcc aga gtc cag ctc tac aac gta gtg ctt cag<br>Pro Leu Pro Thr Pro Ala Arg Val Gln Leu Tyr Asn Val Val Leu Gln<br>430                   435                 440 | | 1446 |
| cct cac cag aac ttc ctg ctg ttc ggt gca gac gtt gtc tat aaa<br>Pro His Gln Asn Phe Leu Leu Phe Gly Ala Asp Val Val Tyr Lys<br>445                   450                 455 | | 1491 |
| tgaaggcacc agggtgccg ggggctgtca gccgcacctg ttcctgatgg gctgtggggc | | 1551 |
| accggctgcc tttccccagg gaatcctctc cagatcttaa ccaagagccc cttgcaaact | | 1611 |
| tcttcgactc agattcagaa atgatctaaa cacgaggaaa cattattcat tggaaaagtg | | 1671 |
| catggtgtgt attttaggga ttatgagctt ctttcaaggg ctaaggctgc agagatattt | | 1731 |
| cctccaggaa tcgtgtttca attgtaacca agaaatttcc atttgtgctt catgaaaaaa | | 1791 |
| aacttctggt ttttttcatg tg | | 1813 |

```
<210> SEQ ID NO 13
<211> LENGTH: 487
<212> TYPE: PRT
<213> ORGANISM: human

<400> SEQUENCE: 13

Met Arg Glu Asn Met Ala Arg Gly Pro Cys Asn Ala Pro Arg Trp Val
    -30             -25                 -20             -15

Ser Leu Met Val Leu Val Ala Ile Gly Thr Ala Val Thr Ala Ala Val
            -10                  -5                  -1   1

Asn Pro Gly Val Val Arg Ile Ser Gln Lys Gly Leu Asp Tyr Ala
                5                  10                  15

Ser Gln Gln Gly Thr Ala Ala Leu Gln Lys Glu Leu Lys Arg Ile Lys
        20                  25                  30

Ile Pro Asp Tyr Ser Asp Ser Phe Lys Ile Lys His Leu Gly Lys Gly
    35                  40                  45

His Tyr Ser Phe Tyr Ser Met Asp Ile Arg Glu Phe Gln Leu Pro Ser
50                  55                  60                  65

Ser Gln Ile Ser Met Val Pro Asn Val Gly Leu Lys Phe Ser Ile Ser
            70                  75                  80

Asn Ala Asn Ile Lys Ile Ser Gly Lys Trp Lys Ala Gln Lys Arg Phe
            85                  90                  95

Leu Lys Met Ser Gly Asn Phe Asp Leu Ser Ile Glu Gly Met Ser Ile
        100                 105                 110

Ser Ala Asp Leu Lys Leu Gly Ser Asn Pro Thr Ser Gly Lys Pro Thr
        115                 120                 125

Ile Thr Cys Ser Ser Cys Ser Ser His Ile Asn Ser Val His Val His
130                 135                 140                 145

Ile Ser Lys Ser Lys Val Gly Trp Leu Ile Gln Leu Phe His Lys Lys
                150                 155                 160

Ile Glu Ser Ala Leu Arg Asn Lys Met Asn Ser Gln Val Cys Glu Lys
            165                 170                 175

Val Thr Asn Ser Val Ser Ser Lys Leu Gln Pro Tyr Phe Gln Thr Leu
        180                 185                 190

Pro Val Met Thr Lys Ile Asp Ser Val Ala Gly Ile Asn Tyr Gly Leu
    195                 200                 205

Val Ala Pro Pro Ala Thr Thr Ala Glu Thr Leu Asp Val Gln Met Lys
210                 215                 220                 225

Gly Glu Phe Tyr Ser Glu Asn His His Asn Pro Pro Phe Ala Pro
                230                 235                 240

Pro Val Met Glu Phe Pro Ala Ala His Asp Arg Met Val Tyr Leu Gly
            245                 250                 255

Leu Ser Asp Tyr Phe Phe Asn Thr Ala Gly Leu Val Tyr Gln Glu Ala
        260                 265                 270

Gly Val Leu Lys Met Thr Leu Arg Asp Asp Met Ile Pro Lys Glu Ser
    275                 280                 285

Lys Phe Arg Leu Thr Thr Lys Phe Phe Gly Thr Phe Leu Pro Glu Val
290                 295                 300                 305

Ala Lys Lys Phe Pro Asn Met Lys Ile Gln Ile His Val Ser Ala Ser
                310                 315                 320

Thr Pro Pro His Leu Ser Val Gln Pro Thr Gly Leu Thr Phe Tyr Pro
            325                 330                 335

Ala Val Asp Val Gln Ala Phe Ala Val Leu Pro Asn Ser Ser Leu Ala
        340                 345                 350
```

```
Ser Leu Phe Leu Ile Gly Met His Thr Thr Gly Ser Met Glu Val Ser
    355             360             365

Ala Glu Ser Asn Arg Leu Val Gly Glu Leu Lys Leu Asp Arg Leu Leu
370             375             380                     385

Leu Glu Leu Lys His Ser Asn Ile Gly Pro Phe Pro Val Glu Leu Leu
            390             395                 400

Gln Asp Ile Met Asn Tyr Ile Val Pro Ile Leu Val Leu Pro Arg Val
            405             410             415

Asn Glu Lys Leu Gln Lys Gly Phe Pro Leu Pro Thr Pro Ala Arg Val
        420             425             430

Gln Leu Tyr Asn Val Val Leu Gln Pro His Gln Asn Phe Leu Leu Phe
    435             440             445

Gly Ala Asp Val Val Tyr Lys
450             455
```